(12) United States Patent
Fontayne et al.

(10) Patent No.: US 6,616,594 B2
(45) Date of Patent: Sep. 9, 2003

(54) CARTRIDGE-MOVEABLE SHIELD

(75) Inventors: Diego Y. Fontayne, Montebello, NY (US); Daniel E. Ueda, Cliffside Park, NJ (US); Edward J. Kaplan, Boca Raton, FL (US); Steven S. Ravins, Oyster Bay Cove, NY (US); Ernest A. Elgin, III, Franklin Lakes, NJ (US)

(73) Assignee: Integrated Implant Systems, L.L.C., Arlington, VA (US)

( * ) Notice: Subject to any disclaimer, the term of this patent is extended or adjusted under 35 U.S.C. 154(b) by 0 days.

(21) Appl. No.: 09/858,653

(22) Filed: May 17, 2001

(65) Prior Publication Data

US 2002/0032360 A1 Mar. 14, 2002

Related U.S. Application Data

(60) Provisional application No. 60/205,055, filed on May 18, 2000.

(51) Int. Cl.[7] ............................................. A61M 37/00
(52) U.S. Cl. ................. 600/7; 604/57; 604/59; 604/60; 604/62; 600/3; 600/8; 600/1; 600/2; 600/104; 600/108
(58) Field of Search ................. 600/1, 2, 3, 7, 600/8; 604/57, 59, 60, 62

(56) References Cited

U.S. PATENT DOCUMENTS

| | | |
|---|---|---|
| 3,704,707 A | 12/1972 | Halloran |
| 4,267,149 A | 5/1981 | Bruckner et al. |
| 4,400,170 A | 8/1983 | McNaughton et al. |
| 4,451,254 A | 5/1984 | Dinius et al. |
| 4,474,572 A | 10/1984 | McNaughton et al. ........ 604/61 |
| 4,700,692 A | 10/1987 | Baumgartner |
| 4,838,265 A | 6/1989 | Cosman et al. |
| 5,242,373 A | 9/1993 | Scott et al. |
| 5,305,203 A | 4/1994 | Raab |
| 5,366,896 A | 11/1994 | Margrey et al. |
| 5,514,101 A | 5/1996 | Schulz et al. |
| 5,609,152 A | 3/1997 | Pellegrino et al. |
| 5,860,909 A | 1/1999 | Mick et al. |
| 5,871,448 A | 2/1999 | Ellard |
| 6,002,859 A | 12/1999 | DiGioia, III et al. |
| 6,007,474 A | 12/1999 | Rydell |
| 6,102,844 A | 8/2000 | Ravins et al. |
| 6,129,670 A | 10/2000 | Burdette et al. |
| 6,206,832 B1 | 3/2001 | Downey et al. |
| 6,214,013 B1 | 4/2001 | Lambrecht et al. |
| 6,270,472 B1 | 8/2001 | Antaki et al. |
| 6,387,034 B1 | 5/2002 | Lee |

FOREIGN PATENT DOCUMENTS

WO 97 22379 6/1997

*Primary Examiner*—Gregory L. Huson
*Assistant Examiner*—Azy Kokabi
(74) *Attorney, Agent, or Firm*—Heller Ehrman White & McAuliffe

(57) ABSTRACT

A cartridge is configured to be inserted into a medical instrument for treating patients with radioactive seeds. The cartridge includes a rotating internal barrel that is loaded with a plurality of seeds, where the internal barrel has a plurality of conduits for accepting the seeds. As the internal barrel rotates, a seed from one of the conduits is deposited into a shuttle, and then the shuttle is fully extended so as to provide the seed to the medical instrument. The shuttle is then retracted, and the barrel is rotated to the next conduit, so as to receive a seed from that next conduit. The cartridge includes a first shield and a second shield, each having slots where the slots of the first and second shields are aligned in a first verification or calibration mode, and where the slots are not aligned in a normal, seed depositing mode. The second shield also includes a plurality of numeric indicators that indicate a current number of seeds remaining in the cartridge.

10 Claims, 52 Drawing Sheets

900

900

900

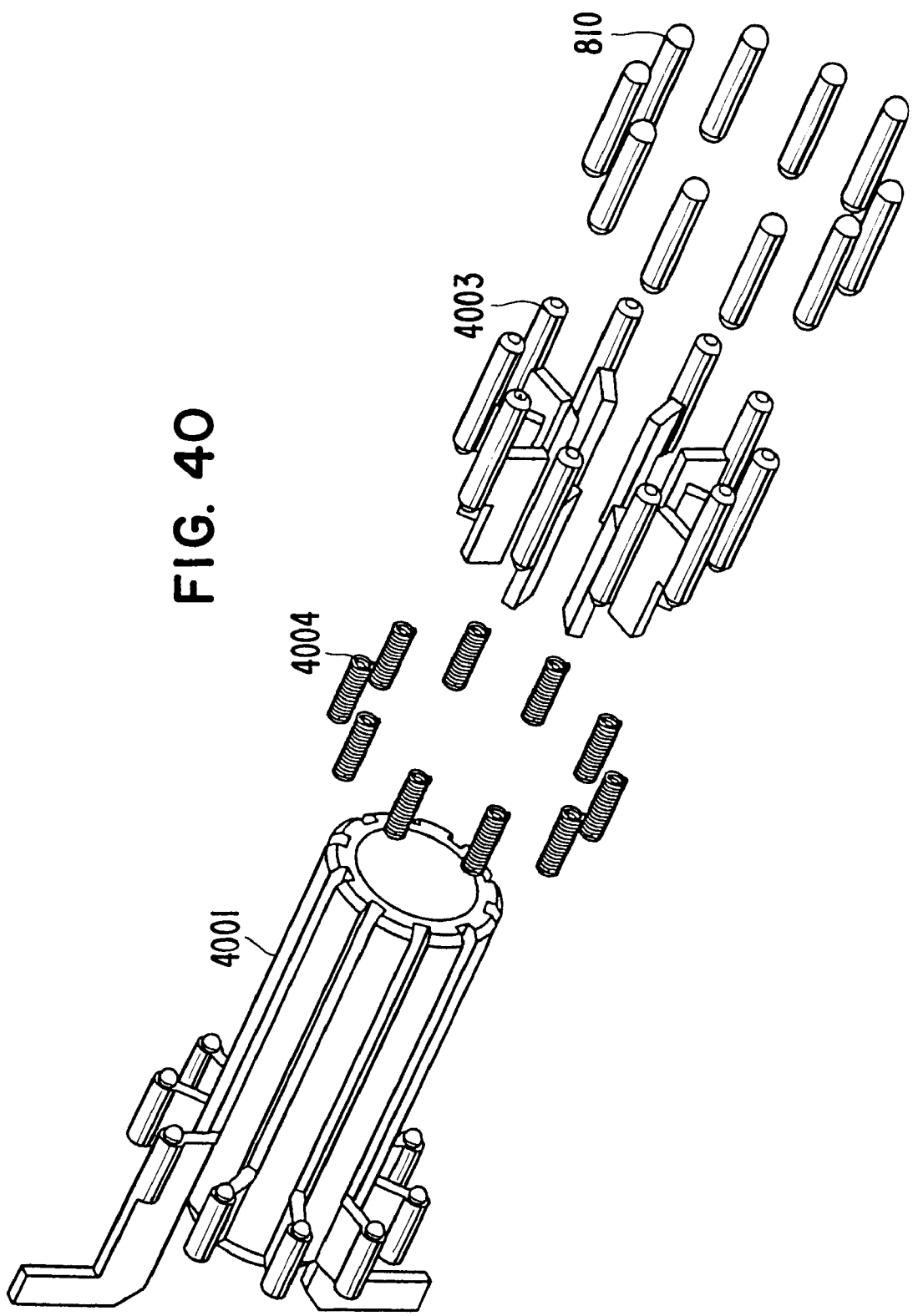

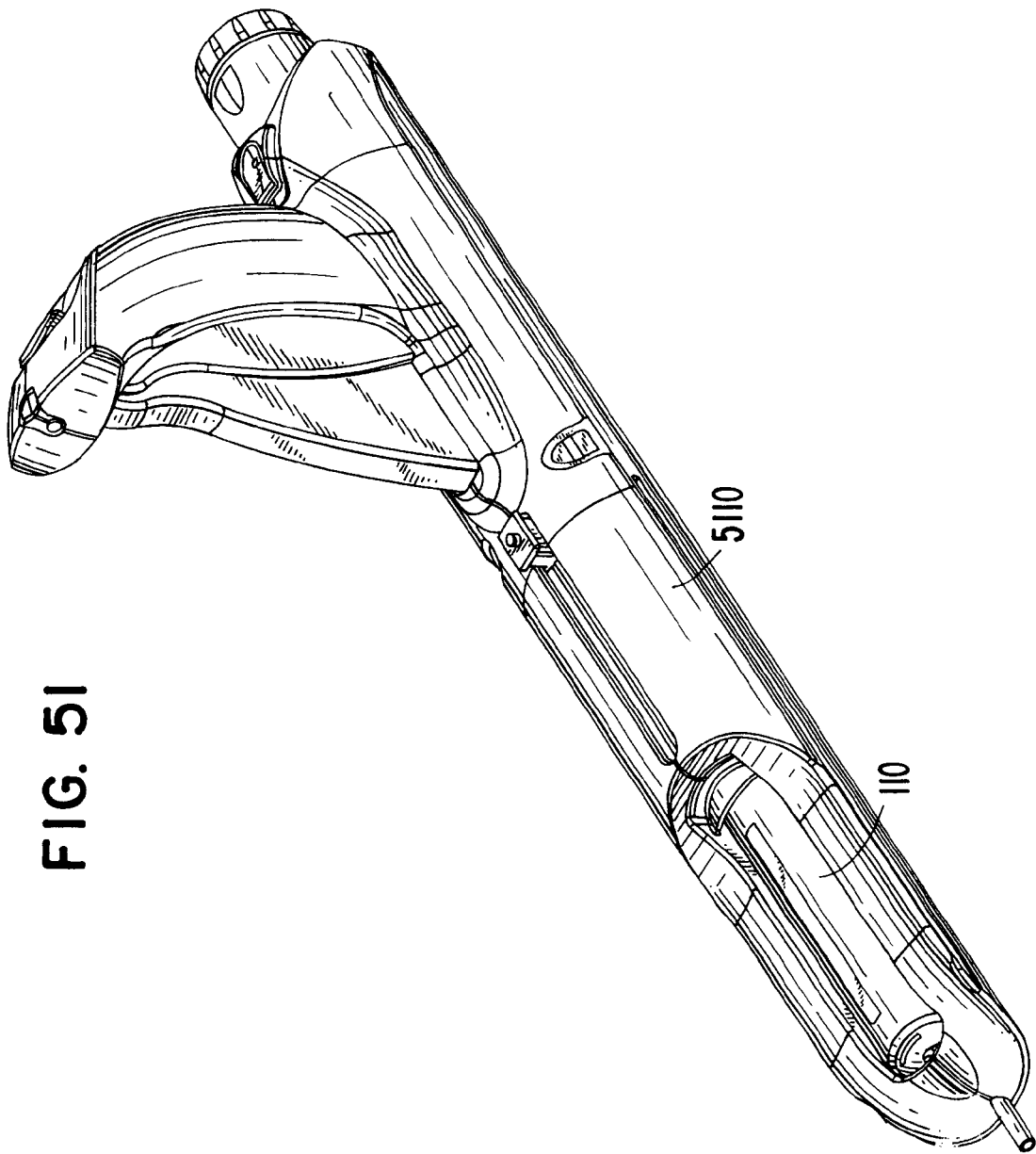

CARTRIDGE-MOVEABLE SHIELD

This application claims priority to U.S. provisional application No. 60/205,055, filed May 18, 2000, which is incorporated in its entirety herein by reference.

BACKGROUND OF THE INVENTION

1. Field of the Invention

The present invention relates to a cartridge that is configured to accept radioactive seeds, to be used in medical treatment of a patient. In particular, the present invention relates to a cartridge that allows for a plurality of radioactive seeds to be stored within the cartridge, and that is adapted to be fitted within a medical instrument to thereby apply one or more of the radioactive seeds to the patient, one at a time.

2. Description of the Related Art

For treating various medical conditions, such as prostate cancer or tumors, certain treatments involve providing radioactive seeds to particular locations within a patient's body. For example, U.S. patent application Ser. No. 08/763,759, by Steven S. Ravins, Edward Kaplan and Ernest A. Elgin, describes a fiberoptic-guided interstitial seed manual applicator and seed cartridge for applying seeds to a patient. However, that device, as well as other conventional devices, does not allow for a large number of seeds to be inserted into a seed cartridge at the same time, nor do such devices provide a convenient way to determine the remaining number of seeds within the cartridge. Another problem with such conventional devices is that there is no convenient way to test each individual seed within the cartridge to see if each individual seed is still viable.

SUMMARY OF THE INVENTION

One object of the present invention is to provide a seed cartridge that can hold a plurality of seeds.

Another object of the present invention is to provide a dual-shield cartridge structure to allow for either a normal operation mode, or a calibration or verification mode for seeds within the cartridge structure.

Yet another object of the present invention is to provide a mechanism to readily determine a remaining number of seeds within a cartridge.

Still another object of the present invention is to provide a self-contained shielding sufficient for transportation of a cartridge.

BRIEF DESCRIPTION OF THE DRAWINGS

The invention will become more fully apparent from the following detailed description when read in conjunction with the accompanying drawings with like reference numerals indicating corresponding parts throughout, and wherein:

FIG. 40 shows the different elements making up a pusher cartridge assembly, where those elements are shown separated from each other for sake of clarity, according to the present invention;

FIG. 51 shows the cartridge according to the present invention as it is disposed within a medical instrument that provides seeds to a patient, according to the present invention.

DETAILED DESCRIPTION OF THE PREFERRED EMBODIMENT

Figure 1:
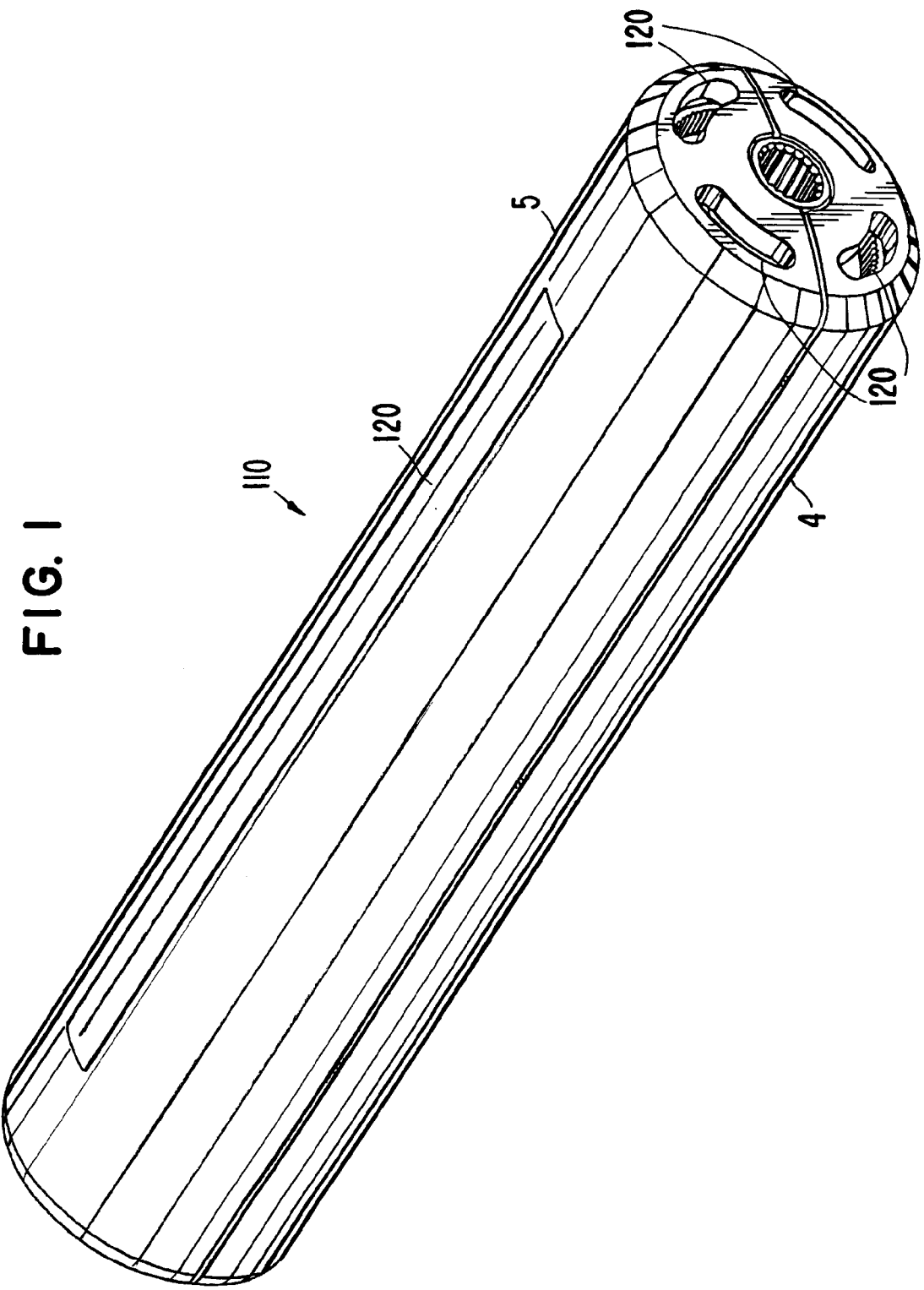
FIG. 1 is a perspective view of the outer housing of a cartridge, according to the present invention.

A preferred embodiment of the present invention will be described in detail hereinbelow, with reference to the drawings. In the drawings, preferred dimensions, in inches, are provided by way of explanation of the present invention and not by way of limitation. In other words, the present invention is directed to a particular method and apparatus and equivalents thereof with respect to a seed cartridge, and not to the exact sizes of the elements that make up a particular cartridge structure.

The present invention is directed to a cartridge that fits within a medical instrument, and which is configured to carry a plurality of seeds. Once inserted within the medical instrument, such as an instrument similar to the fiberoptic-guided interstitial seed manual applicator as described in U.S. patent application Ser. No. 08/763,759, discussed earlier, the seeds can then be inserted, one at a time, to a particular location of the patient's body, such as a tumor located in the patient's lymph nodes. The cartridge according to the present invention is configured to be filled with one or more radioactive seeds, where those seeds are transported out of the cartridge and into the medical instrument, by way of a multiple-conduit, rotating barrel feature of the cartridge.

Details of a medical instrument in which the cartridge according to the present invention that can be fitted into is a subject of a first related application entitled "MEDICAL INSTRUMENT", Provisional Application No. 60/205,053 filed May 18, 2000, which is incorporated in its entirety herein by reference. Details of [A] a targeting fixture on which the medical instrument (with the cartridge inserted therein) can couple to, more particularly, to a cradle unit or a sheath unit of the targeting fixture, is a subject of a first related application entitled "TARGETING FIXTURE", Provisional Application No. 60/205,094 filed May 18, 2000, and a second related application entitled "TARGETING FIXTURE TO A GRID TEMPLATE", Provisional Application No. 60/205,054, filed May 19, 2000, each of which is incorporated in its entirety herein by reference.

FIG. 1 shows a perspective view of an outer housing 110 of the cartridge according to the present invention. The outer housing 110 includes a top housing body 5 and a bottom housing body 4. The outer housing 110 forms a cylindrical shape, where the top and bottom housing bodies 5, 4 are preferably ultrasonically welded together to form a rigid housing structure. That way, the outer housing 110 is robust and cannot be taken apart without destroying the structure. Other ways of providing a rigid housing structure may be envisioned while remaining within the scope of the invention, such as molding the top and bottom halves axially, or by using a cap on each end that adheres the top and bottom halves together and that can be snapped onto the top and bottom halves.

Figure 23A:
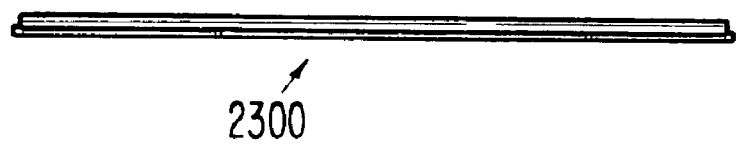
FIGS. 23A–C show different views of a lens body that is configured to fit within an opening of the top housing body of the cartridge, according to the present invention.
Figure 23B:
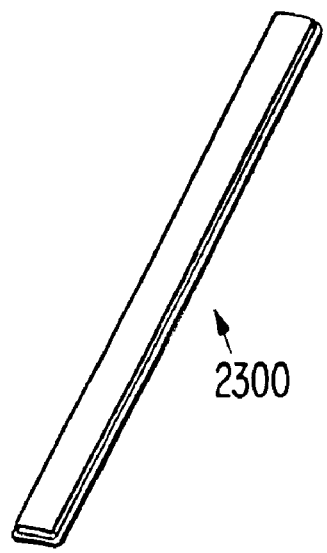
Figure 23C:
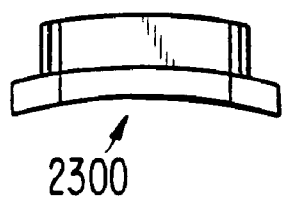

The outer housing 110 allows for ease in rotation of internal components within the housing 110, to be explained in more detail below, while also preventing someone from manipulating components within the housing without proper authorization. The top housing body 5 has a channel or opening 120 provided therein, in which a lens body 2300 (see FIGS. 23A–C) is fitted therein. The lens body 2300 allows a user, such as a doctor or a physicist, to view numeric markings on an outer surface of a tube-scale disposed within the housing 110. The numeric markings indicate a current number of seeds presently disposed within an internal barrel provided within an interior region with respect to the outer housing 110. In the present invention, the outer housing 110 is preferably made of plastic or some other lightweight, non-radiation-attenuating material.

The entire cartridge structure, which includes the outer housing 110, is inserted into a medical instrument (now shown in FIG. 1, but see the cartridge including housing 110 inserted into a medical instrument 5110 in FIG. 51) similar in many respects to how a shotgun cartridge is inserted into a shotgun. The entire cartridge structure is placed into its proper position within the medical instrument. Once the cartridge has been placed into its proper position within the medical instrument, seeds disposed within an internal barrel of the cartridge can be ejected therefrom and into the instrument, where they then can be inserted into a particular location within a patient's body.

Figure 3:
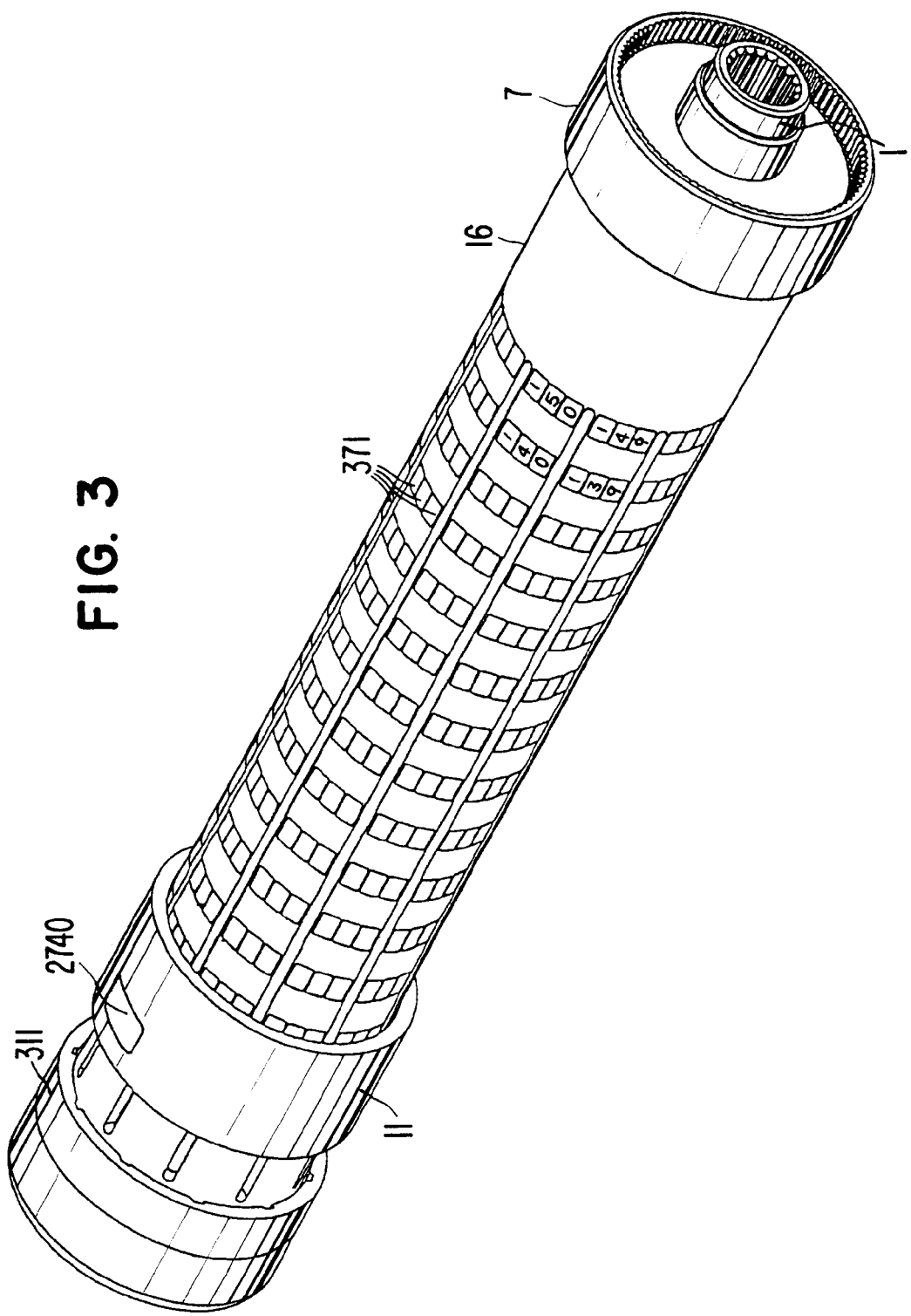
FIG. 3 shows a tube-scale of the cartridge that is provided with numeric indicators, and this figure also shows an indicator ring that is used to display one of the numeric indicators, according to the present invention.

Since the outer housing 110 is made out of non-radiation-attenuating material, some structure located in an interior region with respect to the outer housing 110 must protect a user, such as a doctor or physicist, from radiation emitted by radioactive seeds also located in the interior region. The present invention provides for a tube-scale 16, which is preferably a stainless steel part. FIG. 3 shows the tube-scale 16, which includes a plurality of rectangular areas 371 on the outer surface thereof. In the preferred embodiment, there are 150 separate rectangular areas on the tube-scale 16. Each rectangular area 371 has a specific numeral printed thereon, so as to provide an indication of the current number of seeds currently disposed within the tube-scale 16. The tube-scale 16 thus provides a "scale" function, where an indicator ring 11 that fits around the tube-scale 16 provides an indication of the current number of seeds presently remaining within the cartridge.

Figure 30A:
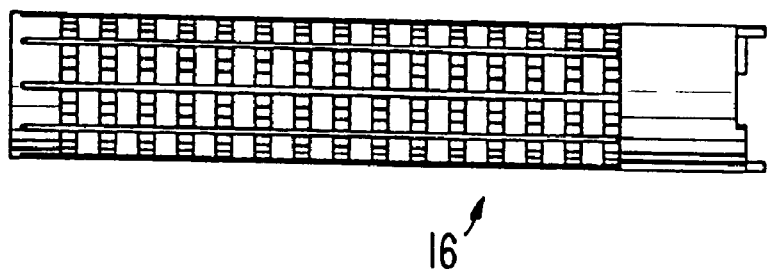
FIGS. 30A–C show different views of a tube-scale, according to the present invention.
Figure 30B:
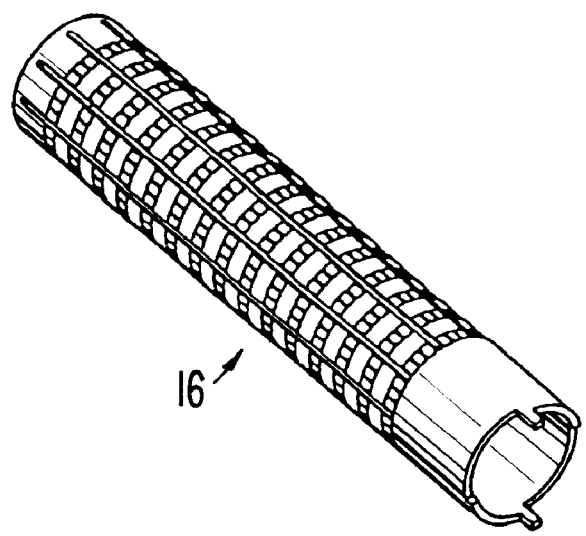
Figure 30C:
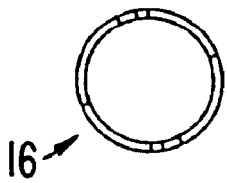

Also shown in FIG. 3 is a proximal cap 7 and a distal cap 311, which are also preferably made of stainless steel to provide strong radiation attenuation (e.g., >99% attenuation) in the axial direction of the cartridge. The tube-scale 16 is preferably at least 0.047" thick, to provide strong attenuation of radiation due to the seeds disposed in an interior region with respect to the tube-scale 16. The tube-scale 16 thus also acts as a "tube", or shield, with respect to radioactive seeds disposed within an internal barrel located in an interior region surrounded by the tube-scale 16. FIGS. 30A–C show different views of the tube-scale 16, which is constructed as a cylindrical ring. The tube-scale 16 includes ten channels or slots that are parallel to each other and that extend from a point close to a first end of the tube-scale 16, to a point close to a second end of the tube-scale 16. The proximal cap 7 and the distal cap 311 are preferably of at least the same thickness as the tube-scale 16.

Figure 26C:
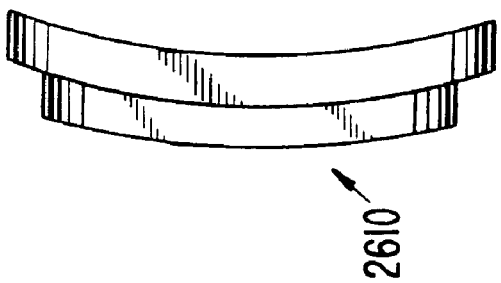
FIGS. 26A–C shows different views of a lens ring, according to the present invention.
Figure 26B:
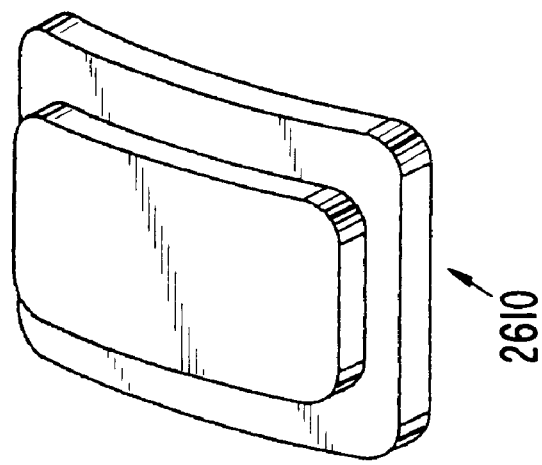
Figure 26A:
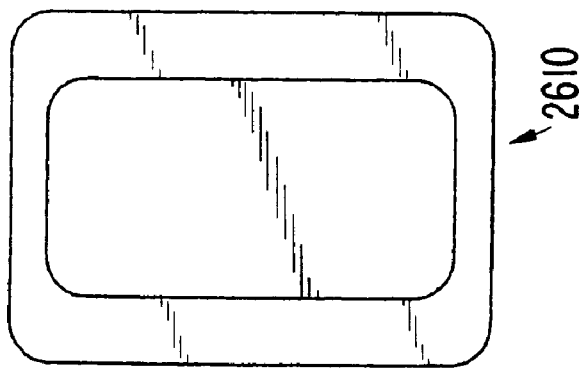
Figure 27C:
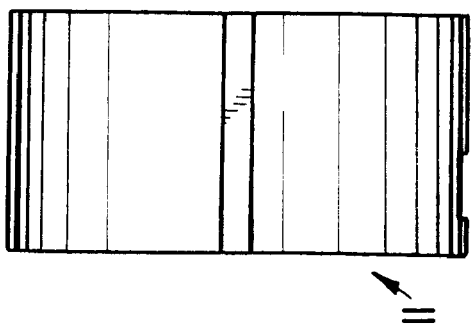
FIGS. 27A–C show different views of the indicator ring, according to the present invention.
Figure 27B:
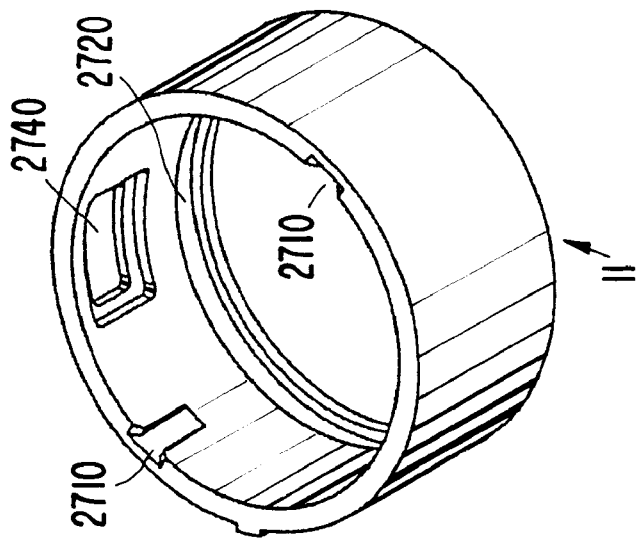
Figure 27A:
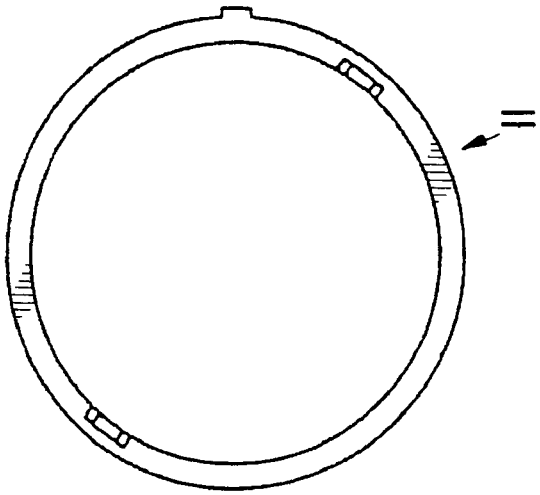

The indicator ring 11 stays fixed rotationally with respect to the tube-scale 16, but it is capable of axially movement with respect to the tube-scale 16. A lens 2610, as seen in FIGS. 26A–C, is fitted within the lens window 2740 of the indicator ring 11 (see also FIG. 27B, and provides some level of magnification to indicate to a user the current number of seeds within the cartridge. The lens 2610 is an optical component, preferably of a clear color and preferably made of plastic or glass, and which provides some level of magnification, e.g., x1.2, x1.5. With the lens 2610 in place, one of the numeric indicators on the outer surface of the tube-scale 16, which is directly below the window of the indicator ring 11, can be readily seen by a user by looking into the channel 120 of the outer housing 110 (see FIG. 1).

Figure 4:
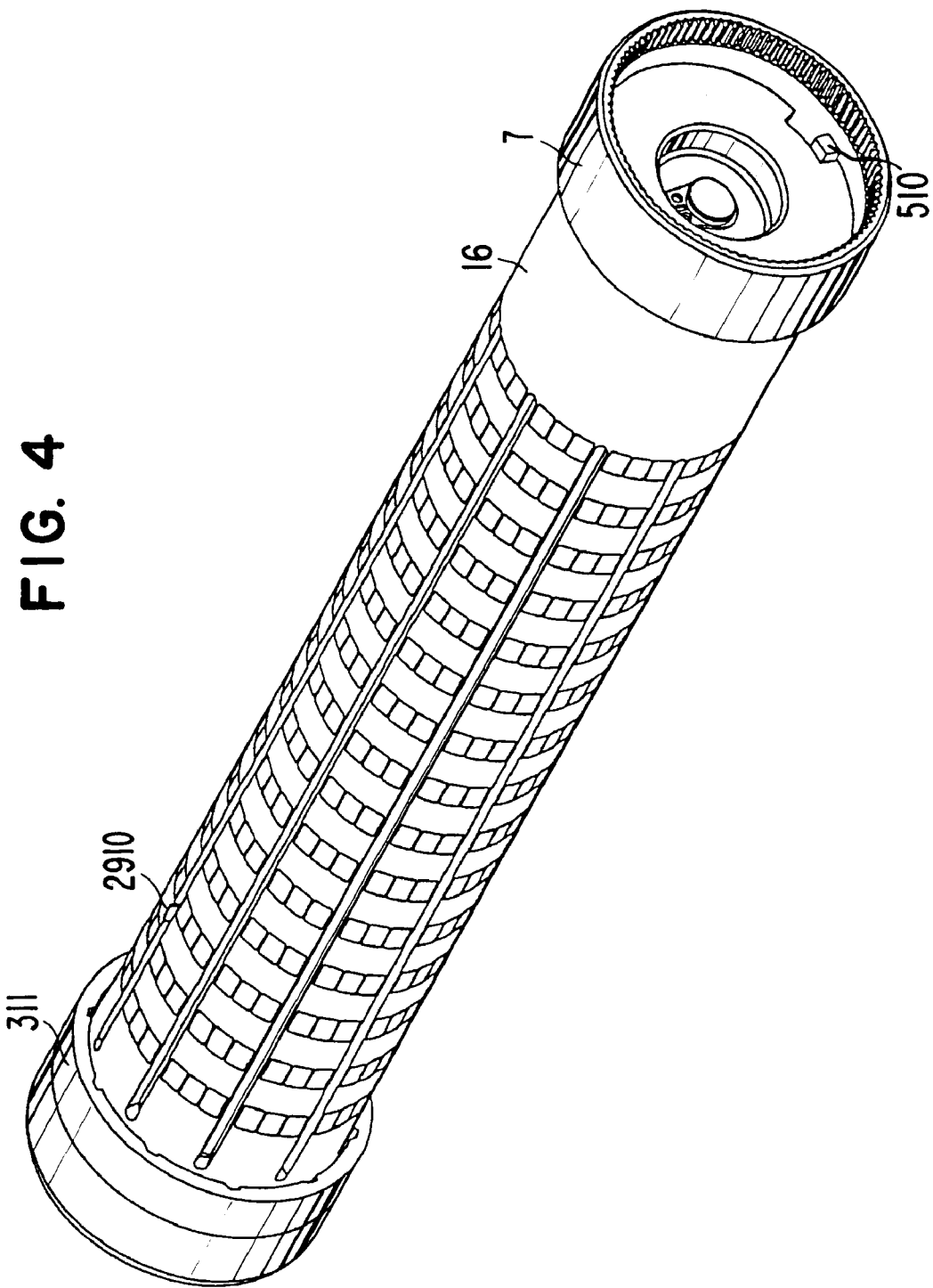
FIG. 4 is a perspective view similar to the view of FIG. 3, but which shows a proximal cap and a slider tab, according to the present invention.
Figure 29A:
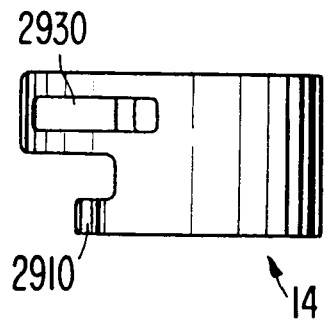
FIGS. 29A–C show different views of a slider indicator, according to the present invention.
Figure 29B:
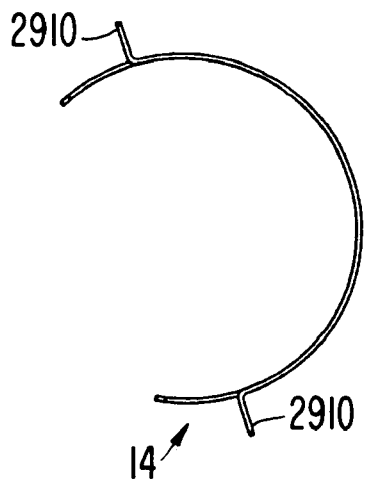
Figure 29C:
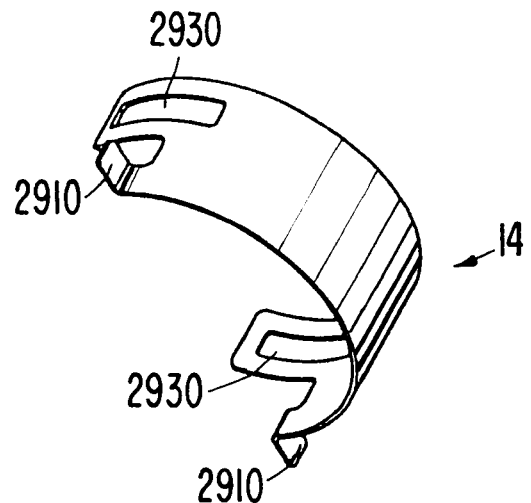

FIG. 4 shows the tube-scale 16 without the indicator ring 11 attached to it, in order to show how the indicator ring 11 moves with respect to the tube-scale 16. A tab 2910 of a slider 14 (see FIGS. 29A–C for the entire structure of the slider 14) slightly sticks out from one of the ten parallel channels of the tube-scale 16.

Figure 14:
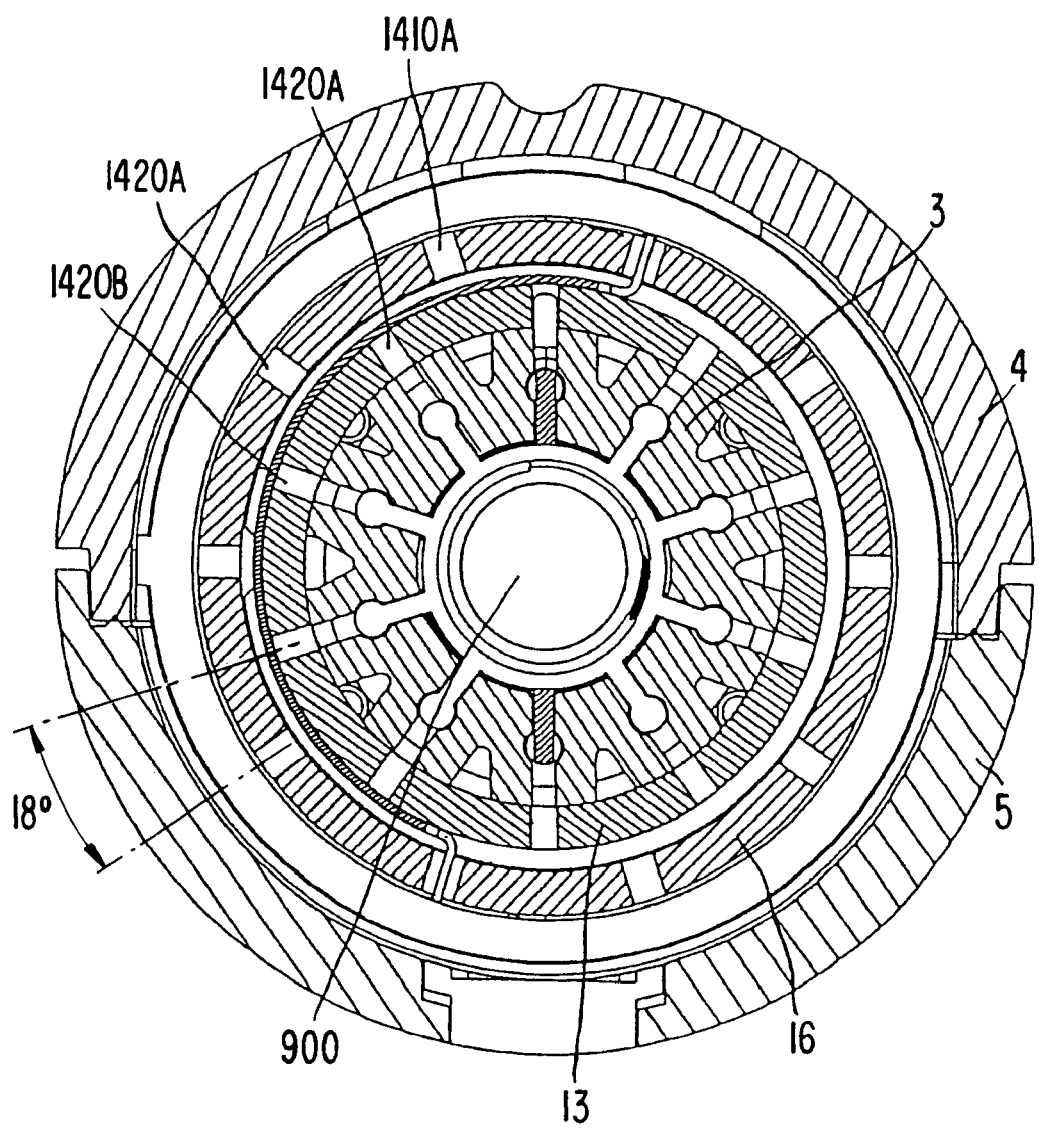
FIG. 14 is a sectional view taken along line A—A of the cartridge of FIG. 13.
Figure 15:
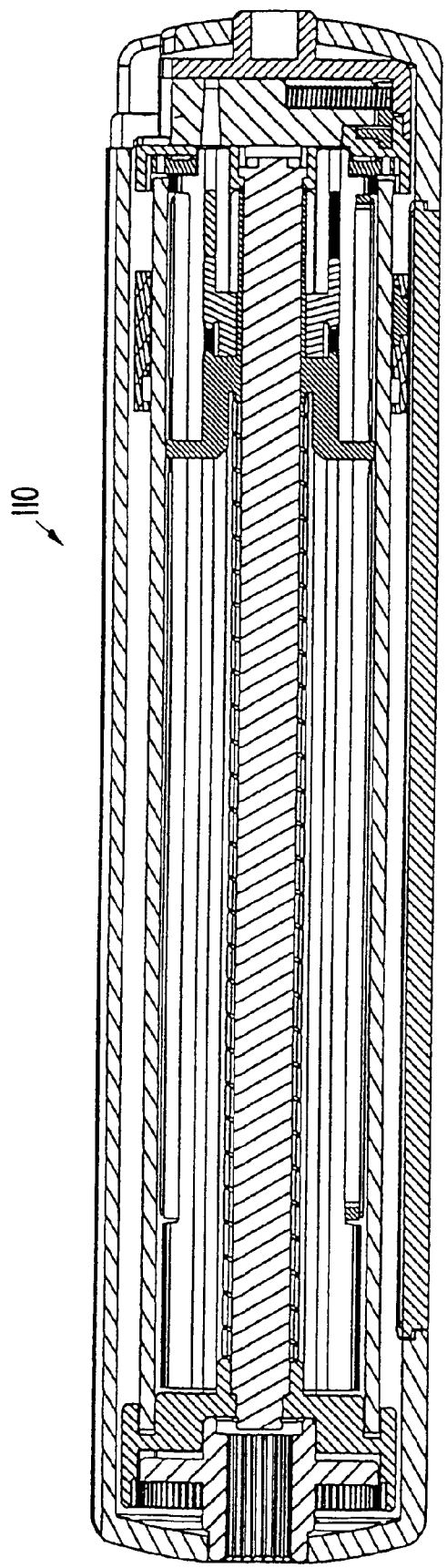
FIG. 15 is a sectional view taken along line B—B of the cartridge of FIG. 13.
Figure 16:
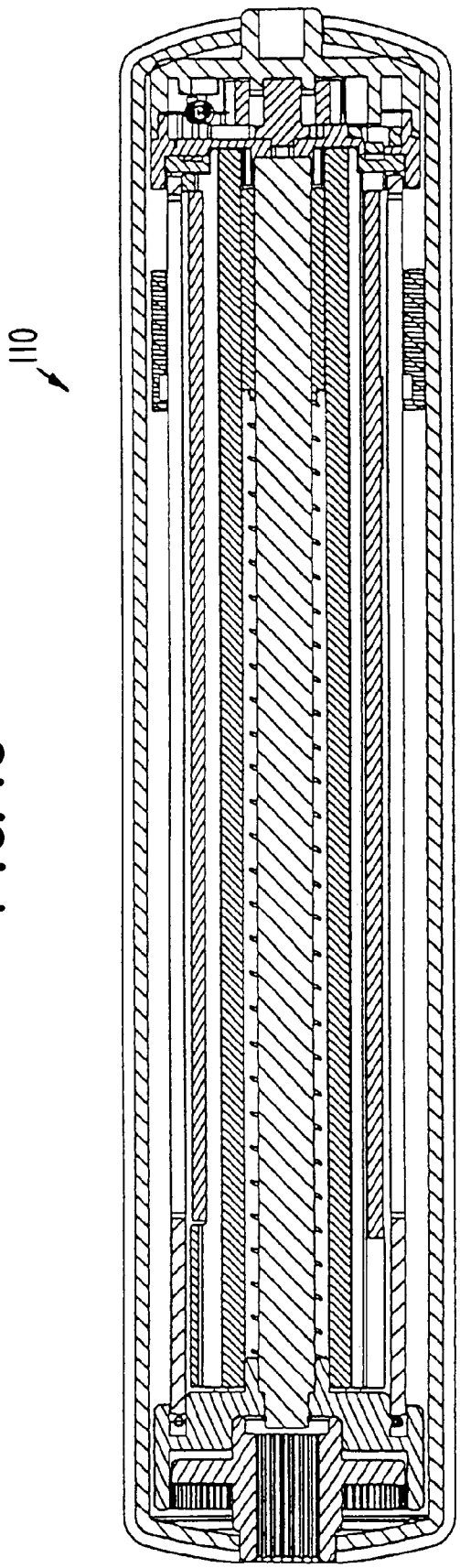
FIG. 16 is a sectional view taken along line C—C of the cartridge of FIG. 13.
Figure 17:
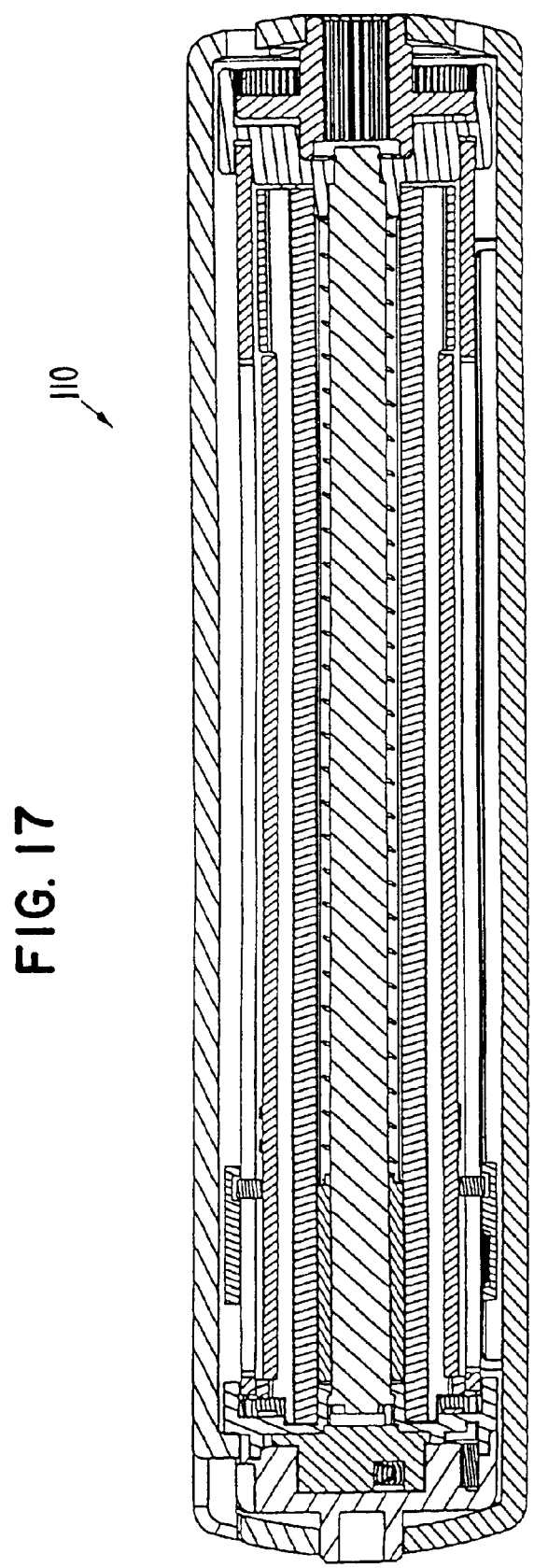
FIG. 17 is a sectional view taken along line D—D of the cartridge of FIG. 13.

Not shown in FIG. 4 are connection springs disposed within the proximal cap 7, and which urge the tube-scale 16 into a normally closed position. In the normally-closed position, the ten parallel channels of the tube-scale 16 are disposed between the ten parallel channels of a shield barrel 13 that is located within an interior region surrounded by the tube-scale 16. This disposition can be seen best in the cross-sectional view of FIG. 14, where the channels or slots (two of the channels are labeled in FIG. 14 as 1420A, 1420B) of the shield barrel 13 are positioned between the channels or slots (two labeled of the channels are labeled in FIG. 14 as 1410A, 1410B) of the tube-scale 16. In this normally-closed configuration, radiation energy from seeds disposed within an internal barrel that is provided in an interior region with respect to the shield barrel 13 is prevented from escaping through the slots of the tube-scale 16. This blocking is due to radiation energy being very collimated, and thus any radiation exiting the slots of the shield barrel 13 are blocked by the continuous stainless steel structure of the tube-scale 16 disposed directly above those slots of the shield barrel 13.

In a verification or calibration mode, the slots of the tube-scale 16 are aligned with the slots of the shield barrel 13, whereby radiation passes through those two sets of slots, through the plastic housing 110 (the radiation passes unattenuated right through the plastic housing 110), and thereby external to the outer housing 110, whereby tests can be performed to determine whether any of the seeds disposed within the cartridge are defective. The discussion of the test or calibration mode and the device used to set the shield barrel 13 and the tube-scale 16 to the test or calibration mode position is outside the scope of the present invention.

Figure 24A:
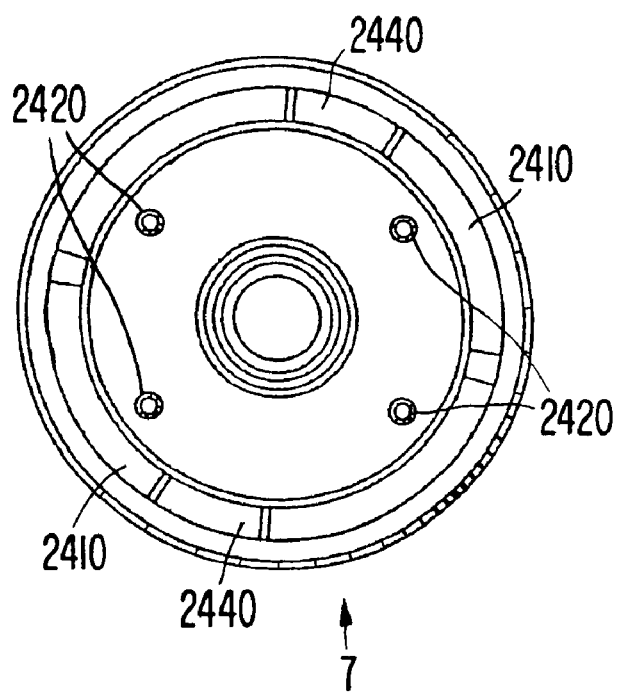
FIGS. 24A–C show different views of a proximal cap, according to the present invention.
Figure 24B:
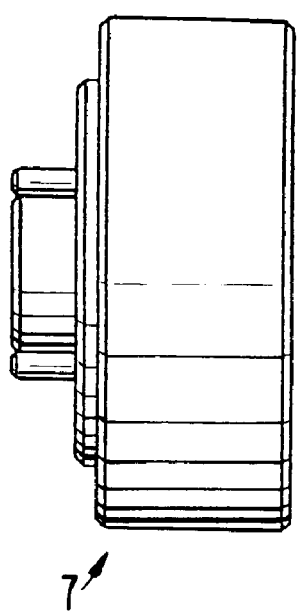
Figure 24C:
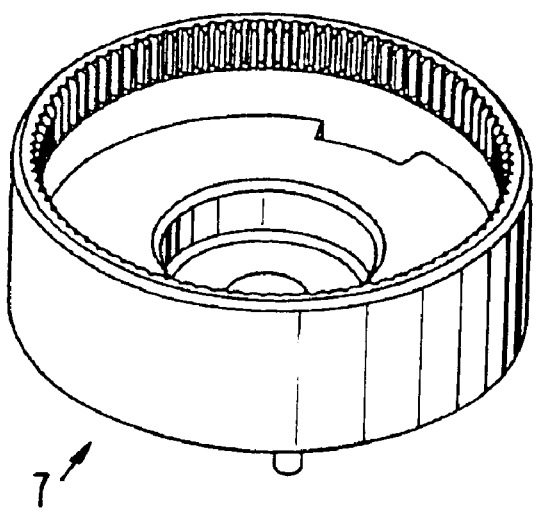
Figure 25A:
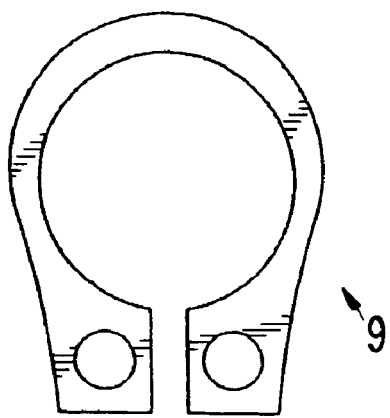
FIGS. 25A–C show different views of a retainer ring, according to the present invention.
Figure 25B:
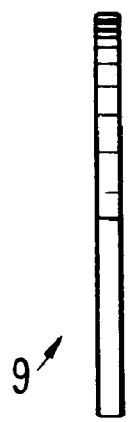
Figure 25C:
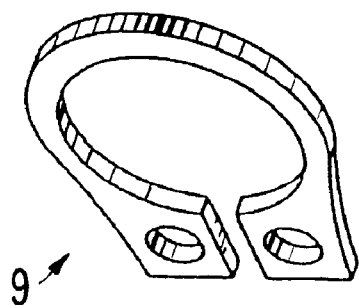
Figure 50C:
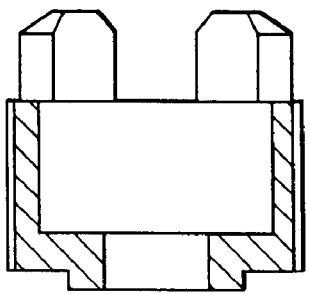
FIGS. 50A–C show different views of a tool which can be used to set the cartridge in place within a device to then be able to set the cartridge the calibration or verification mode with another tool.
Figure 50B:
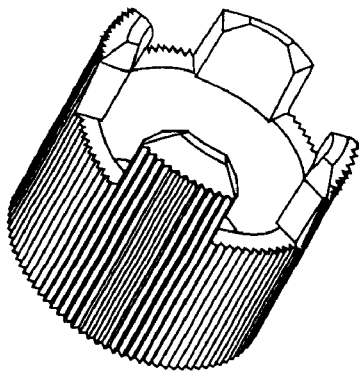
Figure 50A:
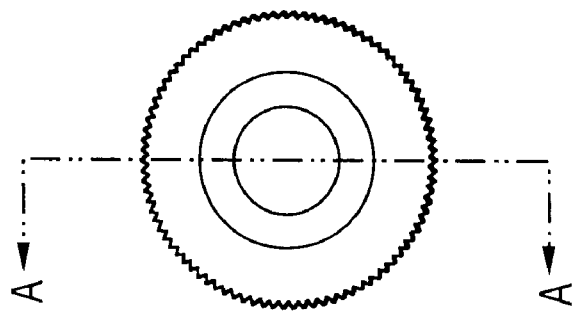
Figure 52B:
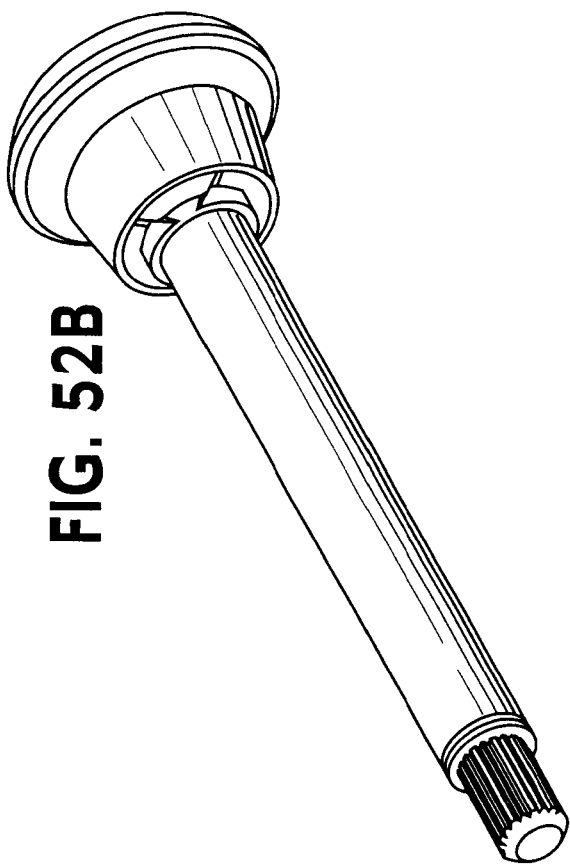
FIGS. 52A–C show different views of a tool that is used to set the cartridge in the calibration or verification mode, once the cartridge has been set in place with the tool of FIGS. 50A–C.
Figure 52C:
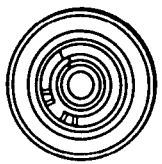
Figure 52A:
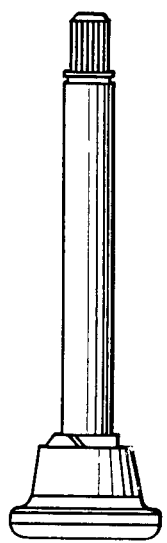

FIG. 1 shows four openings 120 at one side of the outer housing 110, where a four-pronged tool 5000, as shown in FIGS. 50A–C, is configured to fit within those openings 120 to hold the cartridge in place within a device. Once the cartridge is held in place, another tool 5100 can be used to set the shield barrel 13 and the tube-scale 16 in the verification or calibration position, with that other tool 5100 shown in FIGS. 52A–C. Referring to FIGS. 3 and 4, the tool 5000 has teeth that engage with teeth of the proximal cap 7, as shown in FIG. 24C. The tool 5100 fits into the teeth of the adaptor 1 and can be engaged so as to turn the adaptor 1 counterclockwise. This causes a tab 510 of the tube-scale 16 that extends out from a top and bottom opening in the proximal cap 7 (only a bottom tab 510 is shown in FIG. 4) to move counterclockwise. With the adaptor 1 so turned, the slots of the tube-scale 16 are lined up directly above the slots of the shield barrel 13.

Figure 9:
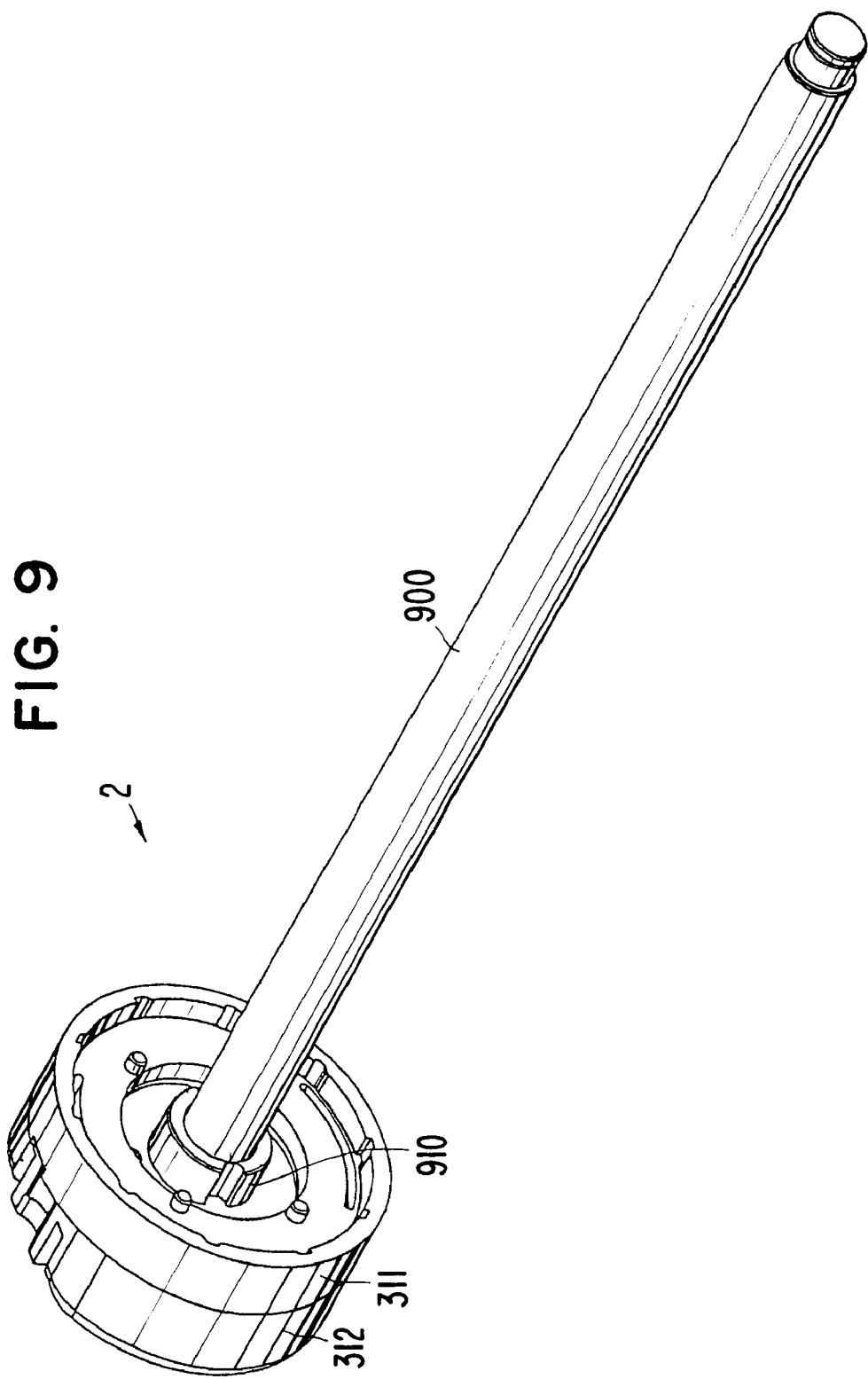
FIG. 9 is a perspective view similar to the view of FIG. 8, but with some elements removed, thereby showing a center rod and a barrel index assembly, according to the present invention.

Referring now to FIG. 9, a center rod 900 is disposed at a central position within the housing 110. This central location of the center rod 900 can also be seen in the cross-sectional view of FIG. 2. Also shown in FIG. 9 is a distal cap 311 that is rigidly affixed to the center rod 900, and a shuttle cover 312 that is coupled to the distal cap 311. The center rod 900 and the distal cap 311 are preferably made of stainless steel to prevent radiation from exiting in an improper direction. The shuttle cover 312 is preferably made of plastic or some other light-weight material.

Figure 31:
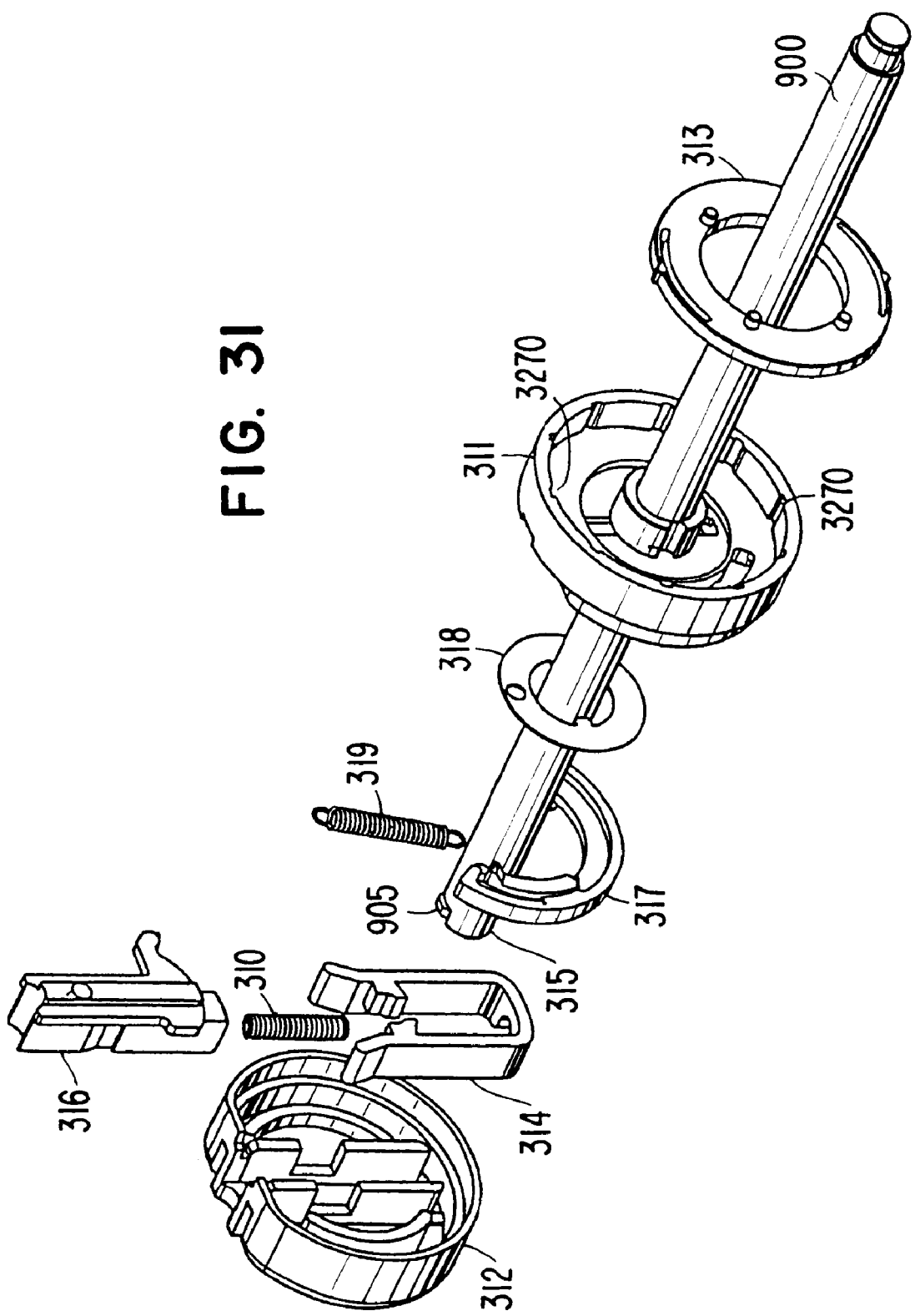
FIG. 31 shows the disposition of various elements making up the barrel index assembly, where those elements are shown apart from each other for sake of clarity, according to the present invention.

The distal cap 311 includes a bearing surface 910, whereby rotation of the internal barrel (and the seeds disposed within the internal barrel) is by way of the bearing surface 910, and not by way of the center rod 900. That is, the center rod 900 stays fixed as the rest of the cartridge rotates. Components within, between and including the shuttle cover 312 and distal cap 311 constitute a barrel index assembly 2, as shown in FIG. 31, to be explained later in more detail.

Figure 7:
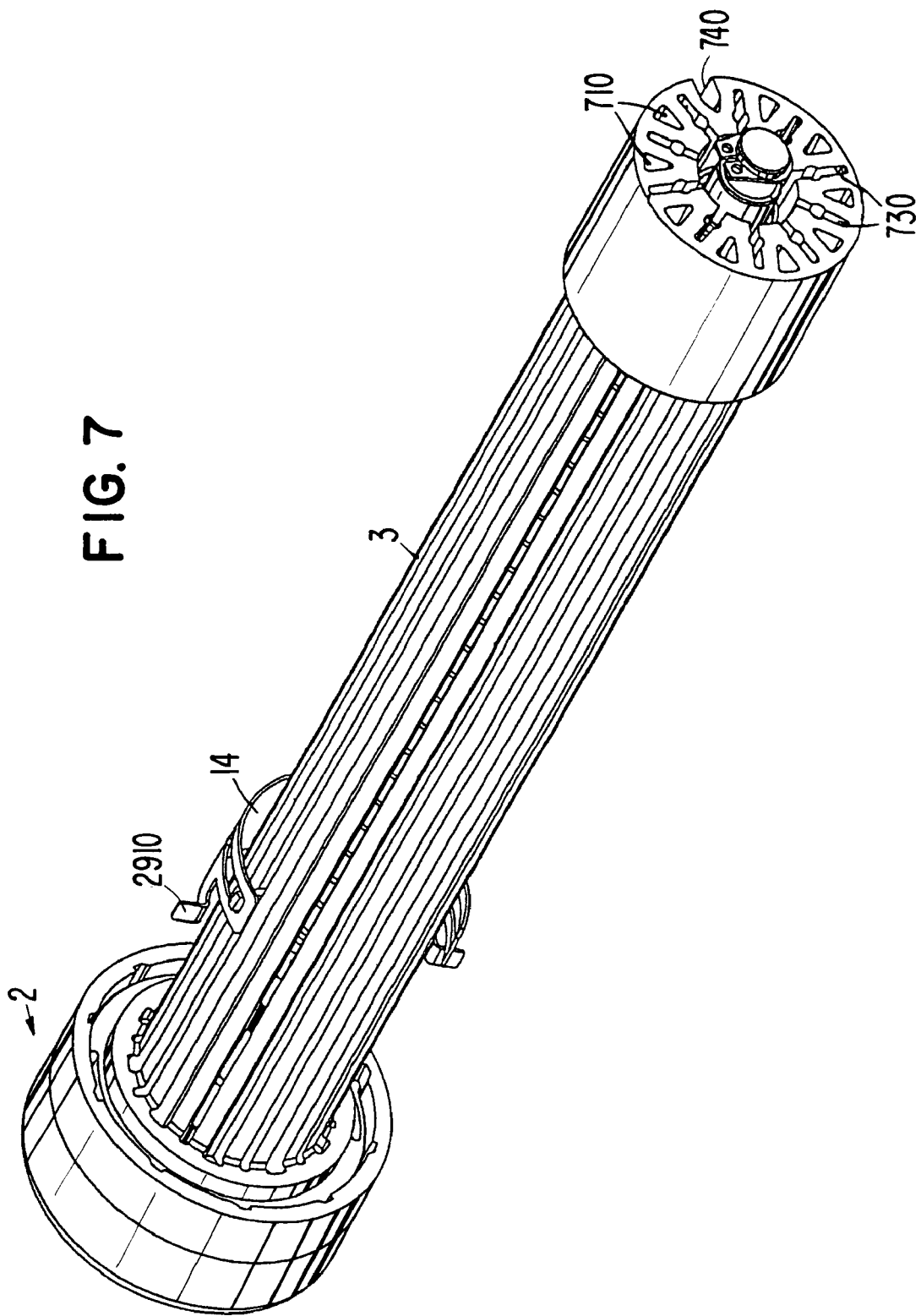
FIG. 7 is a perspective view similar to the view of FIG. 5, but with the shield barrel removed, thereby showing the elements encased by the shield barrel, according to the present invention.
Figure 8:
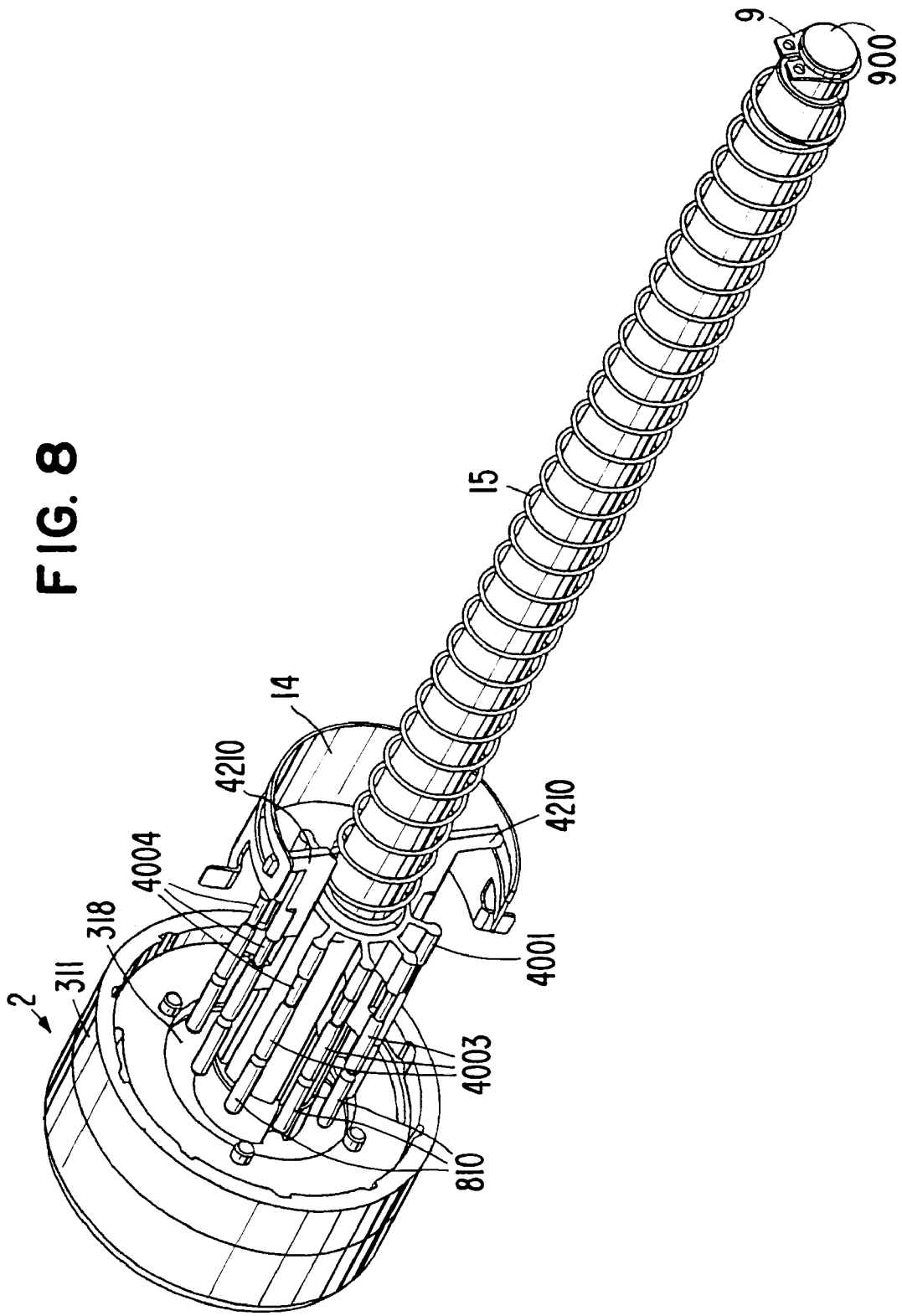
FIG. 8 is a perspective view similar to the view of FIG. 7, but with the internal barrel removed, thereby showing the elements disposed within the internal barrel, according to the present invention.

FIG. 8 shows a pusher spring 15, which is positioned around the center rod 900. A retainer ring 9 is shown as being connected to a proximal end of the center rod 900, and is provided so as to keep one end (a proximal end) of the pusher spring 15 in place. FIG. 7 shows an internal barrel 3, which is fitted over the center rod 900. In the present invention, internal barrel 3 is an extruded part, made from either aluminum or plastic. It is constructed so as to hold up to repeated sterilizations. Methods of extruding plastic or aluminum parts are well known in the art, and will not be discussed herein for sake of brevity so as not to unnecessarily obscure the present invention.

Figure 6:
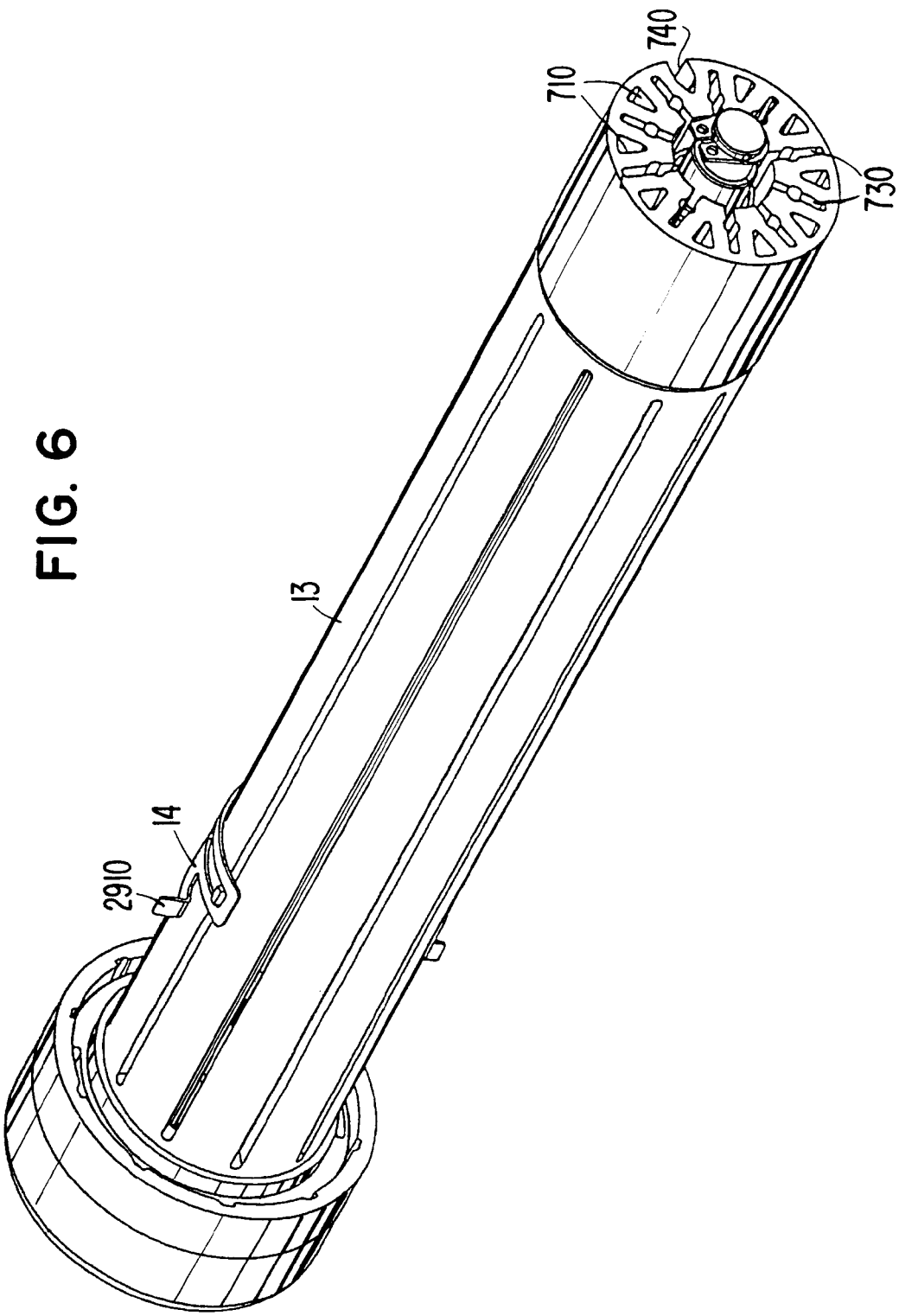
FIG. 6 is a perspective view similar to the view of FIG. 4, but with the tube-scale removed, thereby showing the elements encased by the tube-scale, according to the present invention.
Figure 20B:
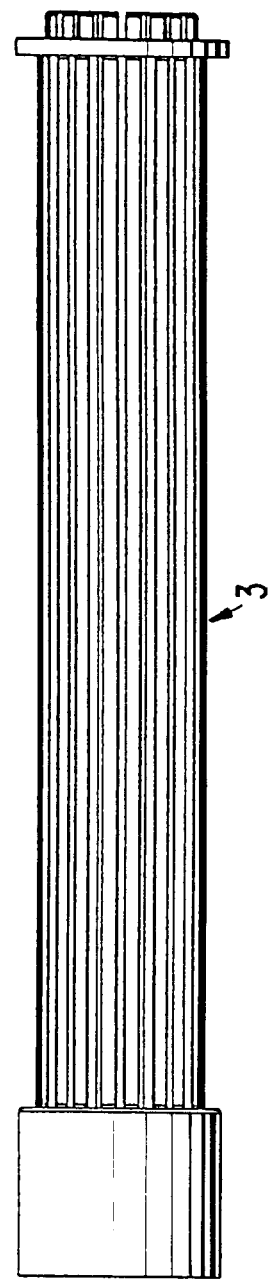
FIGS. 20A–C show different views of an internal barrel, according to the present invention.
Figure 20C:
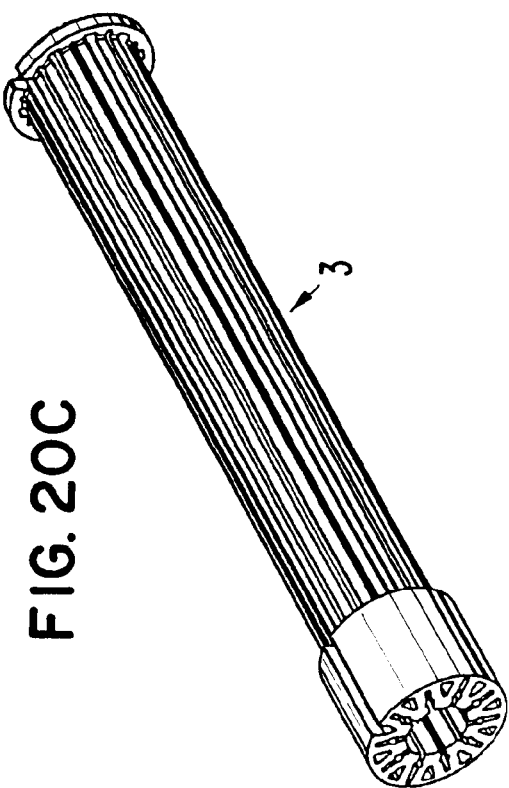
Figure 20A:
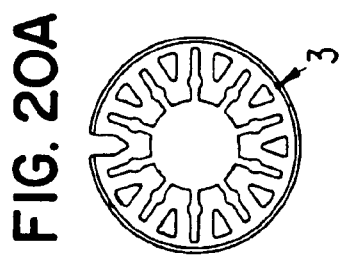
Figure 21A:
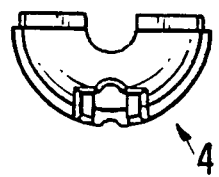
FIGS. 21A–C show different views of a cartridge bottom body, according to the present invention.
Figure 21B:
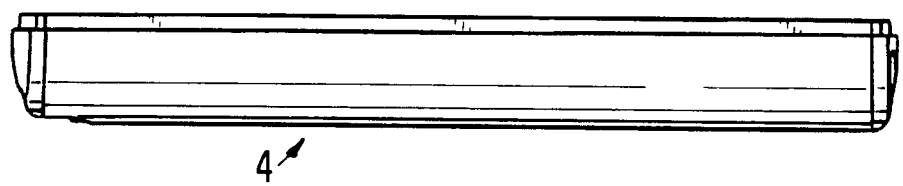
Figure 21C:
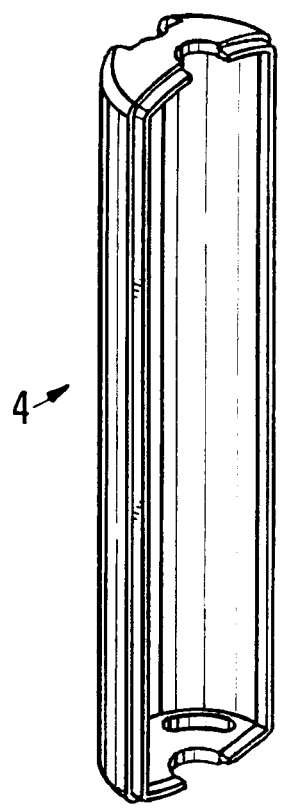
Figure 22A:
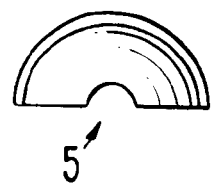
FIGS. 22A–C show different views of a cartridge top body, according to the present invention.
Figure 22B:
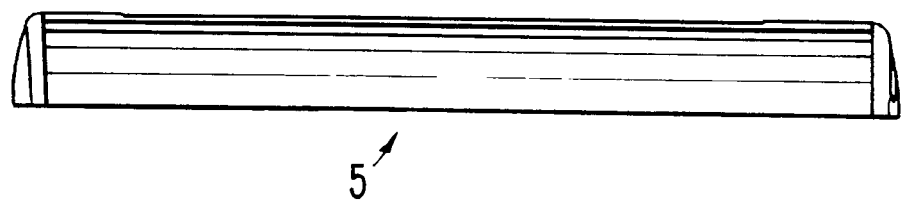
Figure 22C:
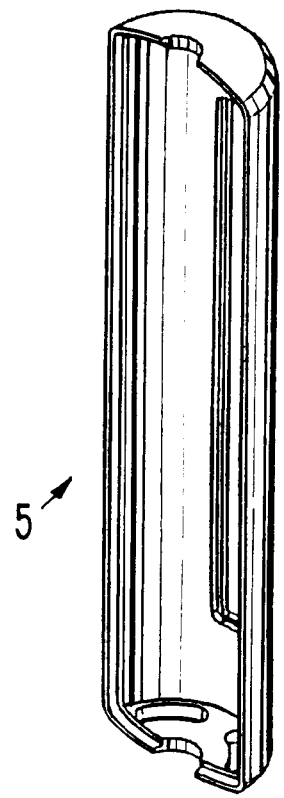

The proximal end of the internal barrel 3 has a plurality of triangular-shaped openings 710, as shown in FIGS. 6, 7 and 20A. Four oppositely-positioned openings 710 are used to accepts pins 2420 of the proximal cap 7, as shown in FIG. 24A. These and the other openings 710 of the internal barrel 3 are used to keep a constant wall thickness for the plastic or aluminum extruded internal barrel 3. The openings 730 are preferable but not mandatory, and are provided due to stability requirements of having the internal barrel 3 being an extruded part. Also shown in FIG. 7 is a tab 740 that extends along the side of the internal barrel 3, and by which the shield barrel 13 and the tube-scale 16 are kept in place with respect to the internal barrel 3, so that they all rotate together.

Figure 42A:
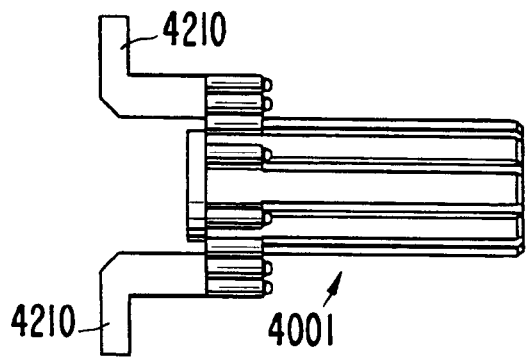
FIGS. 42A–C show different views of a cartridge pusher, according to the present invention.
Figure 42B:
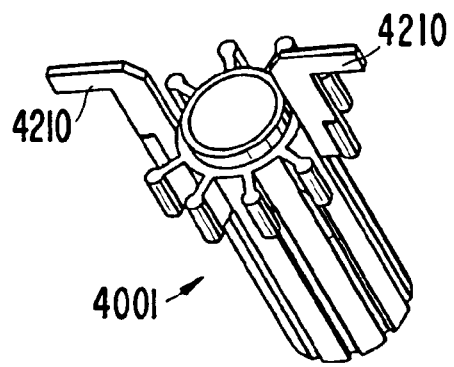
Figure 42C:
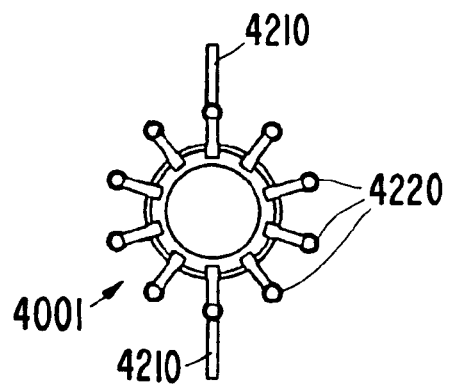

FIG. 7 also shows ten openings 730 having a linear shape with a slightly greater width at a middle portion thereof. The openings 730 extend all the way through the internal barrel 3 from the proximal side to the distal side. The ten openings 730 are sized and positioned to be slightly larger than the size and shape of a cartridge pusher. FIGS. 42A–C show various views of a cartridge pusher 4001, with its ten extensions 4220 that fit into the ten openings 730 of the internal barrel 3. The cartridge pusher 4001 also has two pusher fingers 4210, which are preferably cantilevered beams and which are oppositely-positioned with respect to each other. The two pusher fingers 4210 are positioned within grooves 930 of the slider 14 (see also FIGS. 29A and 29C), as seen in FIG. 8, so that the slider 14 moves in tandem with movement of the cartridge pusher 4001.

Referring now to FIGS. 7, 8 and 40, seeds 810 are placed into each of the ten openings 730 of the internal barrel 3. The internal barrel 3 is sized such that each of the ten openings 730 form respective channels that extend from the proximal end to the distal end of the internal barrel 3, where each can hold up to 15 seeds placed one behind the other in the respective channel. The internal barrel 3 is thus capable of holding up to 150 seeds in its fullest capacity. Of course, other sizes and configurations for the internal barrel 3 may be envisioned while remaining within the scope of the invention.

The first set of ten seeds, with one seed in each opening 730, as shown in FIG. 8, abut against a washer 318 (see also FIGS. 31 and 39A–C). The washer 318 is fitted into tabs of the distal cap 311, as seen best in FIG. 31. The washer 318 has one hole 3910 (see FIGS. 39A and 39C), positioned at the 6 o'clock location when it is fitted into the distal cap 311, by which a front-most seed within the channel having an opening 730 that is facing that hole 3910 is allowed to pass therethrough and into a shuttle (to be described in more detail later).

FIG. 8 also shows seed pushers 4003 that abut against the back-most seeds, with one seed pusher 4003 provided for each of the ten openings 730. FIGS. 40 and 41A–C show the seed pushers 4003 in more detail, whereby each one has a pushing part 4120 and a blocking part 4130. The pushing part 4120 pushes the seeds towards he distal end of the internal barrel 3, so that a seed in the opening 730 that faces the hole 3910 of the washer 318 is forced through the hole 3910 and thereby into a hole of the shuttle. The blocking part 4130 is configured such that, when the last seed in a channel is provided through the hole 3910 in the washer 318, the seed pusher 4003 is prevented from going into the hole 3910 in the washer 318 due to the blocking part 4130 hitting against a portion of the distal cap 311.

The seed pusher 4003 is also configured such that the pushing part 4120 has an extension at its front end that is slightly larger than the width of the hole of the washer 418, and where the extension is tapered inwards, e.g., 45 degree taper. With such a configuration, the tapered part goes partially into the hole 3910 of the washer 318, so as to properly fire the last remaining seed of its respective conduit through the hole 3910 of the washer 318 and into the hole of the shuttle that is disposed at the other side of the washer 318 and distal cap 311. Also, the tapering is provided such that when the shuttle is retracted back to its home position, any part of the seed pusher 4003 that may extend through to the other side of the washer 318 is pushed back by the shuttle towards its conduit in the internal barrel 3. That way, the shuttle does not get caught against a seed pusher 4003 when the shuttle is retracted.

FIG. 8 also shows seed springs 4004, with one seed spring 4004 provided between a respective seed pusher 4003 and the cartridge pusher 4001 in each of the ten channels 730. The ten seed springs 4004 provide the force to push the seed in the opening facing the hole 3910 of the washer 318, through that hole 3910 and into a hole of the shuttle disposed on the other side of the distal cap 311. The hole of the shuttle is configured to accept one seed at a time.

By way of this configuration, with a pusher cartridge assembly 8 that includes one cartridge pusher 4001, ten seed springs 4004, and ten seed pushers 4003, seeds 810 can be provided to the shuttle, one by one, by emptying one seed per row, as the internal barrel 3 rotates. The pusher spring 15 is provided such that the sum of the ten individual seed springs 4004 at their maximum compressed position, is always less than the minimum extended position or force of the pusher spring 15. This guarantees that any number of seeds within any of the ten channels 730 of the internal barrel 3 are compressed against the washer 318.

As seen in FIG. 7, the internal barrel 3 has ten parallel slots that extend at its outermost periphery and that are equally spaced apart from each other. That is, an adjacent two slots are spaced 36 degrees apart. These slots are sized such that the seeds within the channels of the internal barrel 3 cannot fall out of the respective channels 730 by way of the slots. That is, the slots are sized so as to be smaller in width that the width of the seeds.

Referring now to FIG. 8, the slider 14 is coupled to the cartridge pusher 4001, and thus its position is directly related to the current number of seeds 810 remaining in the internal barrel 3. As the seeds empty one by one into the shuttle to be later provided to within a patient's body, the slider 14 rotates accordingly. As a row of ten seeds is emptied one by one into the shuttle, the slider 14 moves in a direction towards the distal end of the internal barrel 3. FIG. 7 shows the slider 14 positioned outside of the internal barrel 3, and FIG. 8 shows that the slider 14 is fitted onto two pusher fingers 4210 of the cartridge pusher 4001. In actuality, slider 14 is positioned outside of the shield barrel 13 as well, but FIG. 7 is provided to more clearly show the relationship of the cartridge pusher 4001 and the slider 14. The pusher fingers 4210 are inserted into the respective openings 730 of the barrel 3 by compressing them to a smaller size, then inserting them in their compressed state into the respective openings 730. Once inside the internal barrel 3, the pusher fingers 4210 will expand back to their normal shape and thereby extend through two oppositely-positioned slots of the internal barrel 3. The pusher fingers 4210 also are sized so that they extend slightly out from two oppositely-positioned slots of a shield barrel 13 that is placed over the internal barrel 3, whereby the pusher fingers 4210 provide contact points for adhering the slider 14 to the cartridge pusher 4001.

FIG. 8 shows the actual configuration with the slider 14 positioned outside of the shield barrel 13. Slider 14 has a tab 2910, as seen also in FIGS. 29A–C, where that tab 2910 extends slightly above one of the channels of the tube-scale 16, as seen best in FIG. 5. The tab 2910 provides the mechanism for correctly positioning the indicator ring 11, as seen in FIG. 3, over the proper numeric indicator provided on the outer surface of the tube-scale 16.

The coupling of the indicator ring 11 onto the tab 2910 of the slider 14 will now be described below with reference to FIGS. 3 and 27A–C. The tab 2910 of the slider 14 is slid over the ramp 2710 of the indicator ring 11. Since there is another tab oppositely-positioned with respect to the tab 2910 shown in FIG. 3, there are two ramps 2710 provided on the indicator ring 11. The tabs 2910 are slid over the ramps 2710, where they pop into place within a groove 2720 that extends around an inner surface of the indicator ring 11. With the indicator ring 11 locked into place with respect to the slider 14, the configuration of FIG. 3 is arrived at.

Referring now to both FIG. 1 and FIG. 3, the indicator ring 11, with the lens 2610 (see FIGS. 26A–C) fitted within the lens window 2740 of the indicator ring 11, is situated directly below the channel or opening 120 on the top of the top cartridge housing 5. The lens 2610 is positioned directly over a numeric indicator provided on the outer surface of the tube-scale 16, where that numeric indicator provides an indication of the total remaining number of seeds within the cartridge. Preferably, the numeric indicators count downwards from the right to the left in FIG. 3, where the right-most row corresponds to the numbers 150-141, the next-to-the-right-most row corresponds to numbers 140-131, and so on. Alternatively, the numeric indicators can count upwards.

Figure 28A:
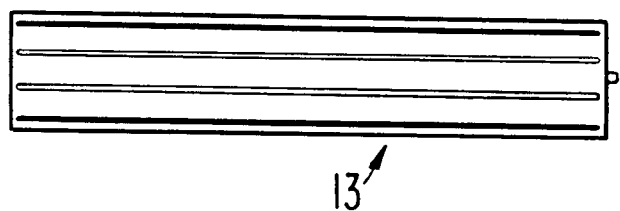
FIGS. 28A–C show different views of a shield barrel, according to the present invention.
Figure 28B:
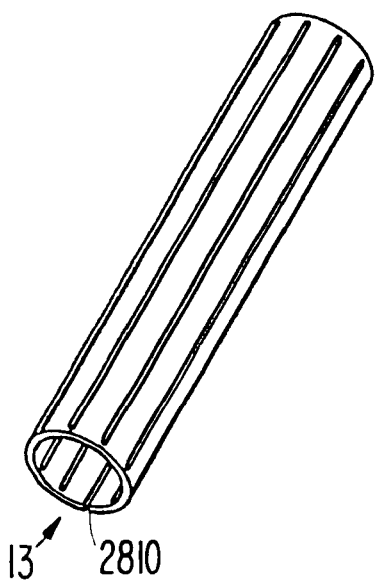
Figure 28C:
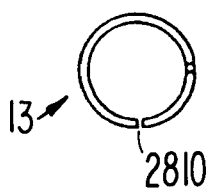

When fitting the components to form the cartridge structure, the internal barrel 3 is fitted onto the center rod 500 (see FIGS. 7 and 8), and then the shield barrel 13 is fitted over the internal barrel 3. Like tube-scale 16, the shield barrel 13 forms a cylindrical shape with an empty interior region. In the preferred embodiment, the shield barrel 13 has ten slots, where one slot (not shown in FIG. 6, but see slot 2810 in FIGS. 28B and C) extends all the way from the distal to the proximal end of the shield barrel 13). As a result, the shield barrel 13 has a C-clip configuration, where it can be spread open by way of the one fully-extended slot. The other nine slots extend from a position close to the distal end to a position close to the proximal end of the shield barrel 13. As explained above, the shield barrel 13 can be spread open at the one fully-extended slot 2810 so as to fit the shield barrel 13 in place over the internal barrel 3. With the shield barrel 3 in place, the indicator ring 11 is fitted to the slider 14, and then the tube-scale 16 is placed so that it is fitted over the shield barrel 3. Next, the indicator ring II is fitted onto the tabs of the slider 14 and onto the tube-scale 16. The proximal cap 7 and the distal cap 311 are also provided at respective ends of the cartridge.

Figure 5:
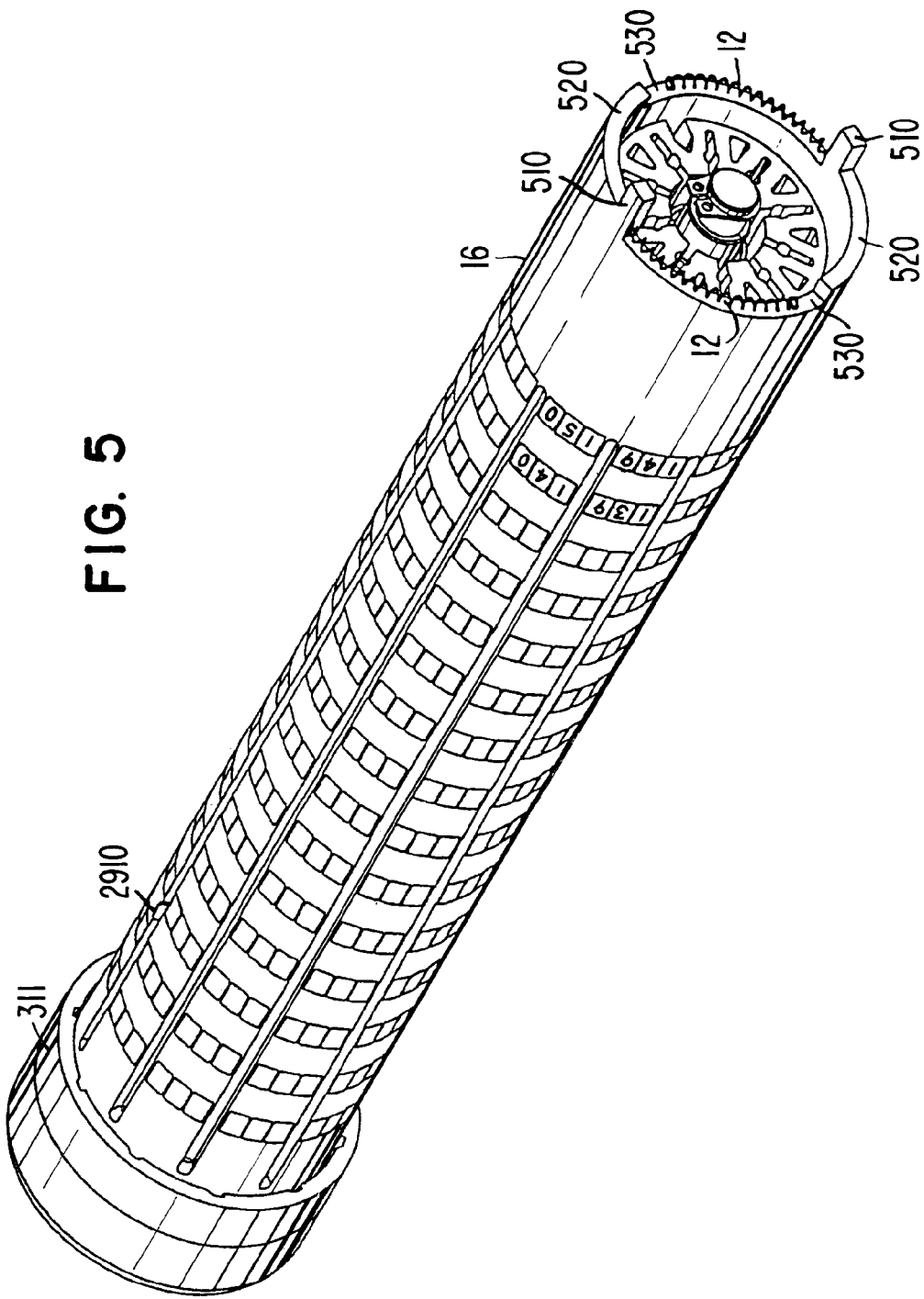
FIG. 5 is a perspective view similar to the views of FIGS. 3 and 4, but which shows compression springs used to bias the tube-scale in the normally-closed position with respect to a shield barrel disposed within the tube-scale, according to the present invention.

The proximal cap 7 is inserted onto the proximal end of the tube scale 16, as seen in FIGS. 4 and 5. Compression springs 12 are provided between the proximal end of the tube scale 16 and the proximal cap 7, so as to urge the tube-scale 16 in a normally-closed position such that the slots of the tube-scale 16 do not line up directly above the slots of the shield barrel 13. In other words, each slot of the tube-scale 16 is disposed 18 degrees apart from the two nearest slots of the shield barrel 13 that is positioned in an interior region with respect to the tube-scale 16.

The two compression springs 12 fit within an area where one end of the tube scale 16 fits with the proximal cap 7. The proximal end of the tube scale 16 has a tab 510, an intermediate surface 520, and a low surface 530, at both the top and bottom of the tube scale 16. The tab 510, the intermediate surface 520 and the low surfaced 530 are preferably laser-burned. The compression springs 12 are nested within the wall thickness of the tube-scale 16. The compression springs 12 are captured within the wall thickness of the tube scale 16, and are held in place when the proximal cap 7 is fitted onto the proximal end of the tube-scale 16. One end of the compression spring 12 rests against the tab 510 of the tube-scale 16, as seen in FIG. 5. The tabs 510 extend slightly outwards from the top and bottom openings of the proximal cap 7, where the tab 510 extending from the bottom opening can be seen in FIG. 4, but where the tab 510 extending from the top opening is obscured due to the viewing angle of FIG. 4.

Figure 18:
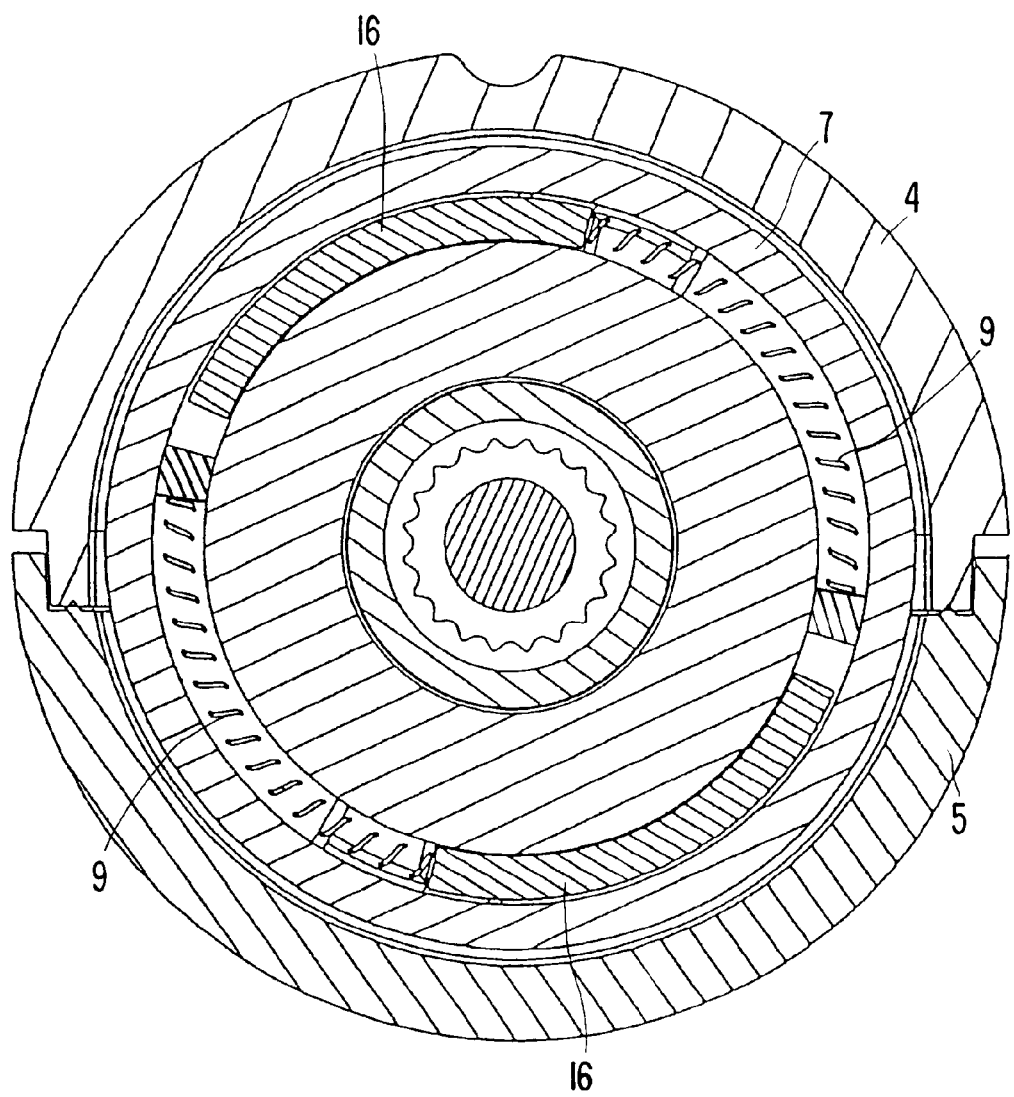
FIG. 18 is a sectional view taken along line E—E of the cartridge of FIG. 13.
Figure 19A:
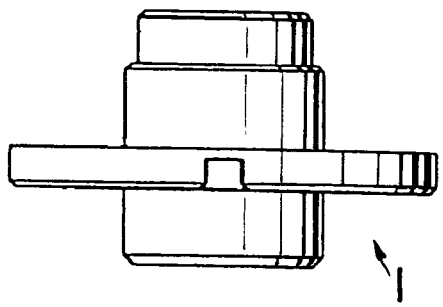
FIGS. 19A–D show different views of an adaptor, according to the present invention.
Figure 19B:
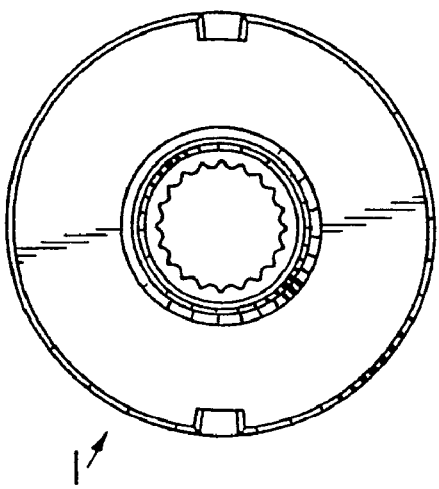
Figure 19C:
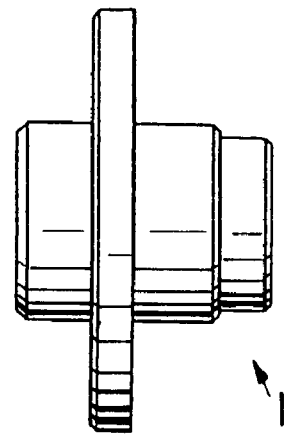
Figure 19D:
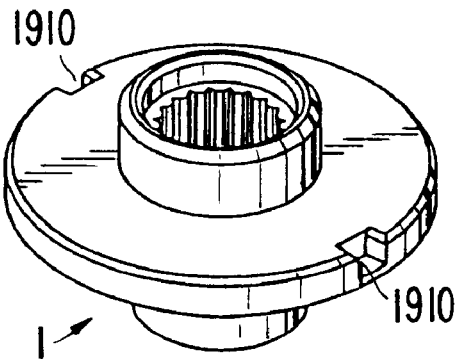

FIG. 18 shows a cross-sectional view of the compression springs 12 being held in place. The wall thickness of the tube-scale 16 is preferably at least 0.047" in thickness, in order to attenuate a high percentage of the radioactive energy of the seeds disposed within the tube scale 16. Each compression spring 12 is preferably less than 0.038" in diameter, and is contained within a respective channel of the proximal cap 7.

As seen in FIG. 24A, channels 2410 are provided on one side of the proximal cap that faces the tube-scale 16. The compression springs 12 force the tab 510 of the tube-scale 16 against one side of the slot of the proximal cap 7, thereby forcing the tube-scale 16 in the closed (non-calibration) position. The tab 510 of the tube-scale 16 extends through slots 2440 of the proximal cap 7, to provide a mechanism for allowing 18 degree movement of the tube-scale 16 relative to the shield barrel 13. This movement is needed to shift the disposition of the tube-scale 16 and the shield barrel 13 for calibration and seed verification purposes. In the preferred embodiment, two compression springs are used for added safety, but it could also be done with one compression spring, if this additional safety feature is not required.

Referring back to FIG. 12, the ring-like structure 1250 at the distal side of the internal barrel 3 is preferably of a diameter greater than the ring-like structure 1260 at the proximal side of the internal barrel 3. This dimensioning is so that the shield barrel 13 may be easily spread apart (as a C-clip) and slid over the internal barrel in a right-to-left direction, with reference to the disposition of elements in FIG. 12. This dimensioning is preferable, but of course the sizes of the two ring-like structures may be set equal to each other in an alternative configuration, if so desired.

As explained above, the internal barrel 3 rotates around the bearing surface 910 of the distal cap, and not on the center rod 900 itself. As seen best in FIG. 14, the center rod 900, which is preferably a stainless steel shaft, prevents radiation from an oppositely-positioned (180 degree) seed channel from exiting in a same direction of a particular seed channel being calibrated/tested, since the steel of the steel-shafted center rod 900 blocks the radiation in that direction. This is useful for the testing and calibration functions performed with the cartridge. The steel of the shield barrel 13 blocks other seed channels from sending their radiation towards a seed channel being tested, since radiation energy is highly directive or collimated. If an odd numbered of channels are used for the internal barrel 3, then this problem would not occur, since there would not be another channel at an opposite, 180 degree, position with respect to a seed channel being tested. For such an odd-numbered channel configuration, a center rod could be used that would not have to attenuate a great majority of the radiation energy of the seeds within the internal barrel 3. Thus, a nine-channel internal barrel constructed in accordance with the present invention could be provided with either a steel center rod or a center rod that does not attenuate radiation energy (such as a plastic center rod). It would also have a shield barrel with nine slots and a tube-scale with nine slots.

FIG. 3 shows an adaptor 1 coupled to the proximal cap 7, and FIG. 4 shows the proximal cap 7 without the adaptor 1 in place. The adaptor 1 has top and bottom tab-accepting slots 1910, as seen in FIGS. 19A–19D, whereby those tab-accepting slots 1910 receive and hold in place the tabs 510 of the tube-scale 16. As explained above, the tabs 510 of the tube-scale 16 extend through openings of the proximal cap 7 and are respectively received within the top and bottom tab-accepting slots 1910 of the adaptor 1.

As explained above, the proximal cap 7 and the distal cap 311 are preferably made out of stainless steel parts, either by metal injection molding (MIM) or made out of powdered metal. They are not made out of plastic because radioactive photons can only be absorbed by high-density materials, such as stainless steel. The higher the density, the higher the attenuation of radioactive energy from being provided externally with respect to the cartridge. MIM and powdered metal manufacturing are processes known to those skilled in the art, and will not be discussed in any detail herein in order to not unnecessarily obscure the present invention. The proximal cap 7 and the distal cap 311 provide a radiation barrier or shield for the proximal and distal ends of the cartridge, with the tube-scale 16 and the shield barrel 13 providing a radiation barrier at the circumferential (curved) portions of the cartridge.

The present invention will now be described with reference to how seeds are provided from the internal barrel 3 and into a shuttle provided at a distal end of the cartridge, to then be provided to a medical instrument to thereby treat a patient with radioactive seeds.

Figure 12:
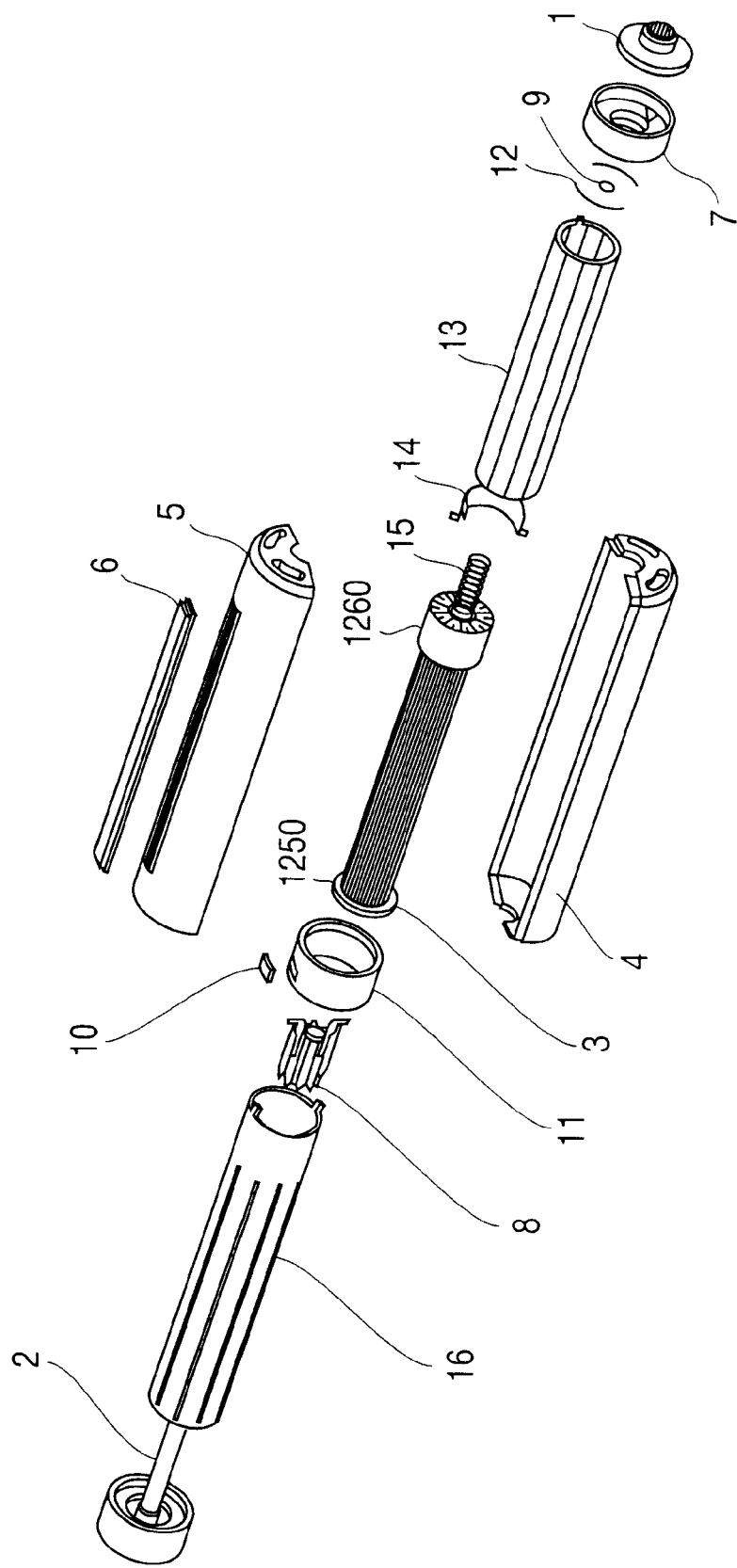
FIG. 12 shows each of the various elements making up the cartridge and the housing of the cartridge, according to the present invention, where those elements are shown separately and not connected together for sake of clarity.
Figure 13:
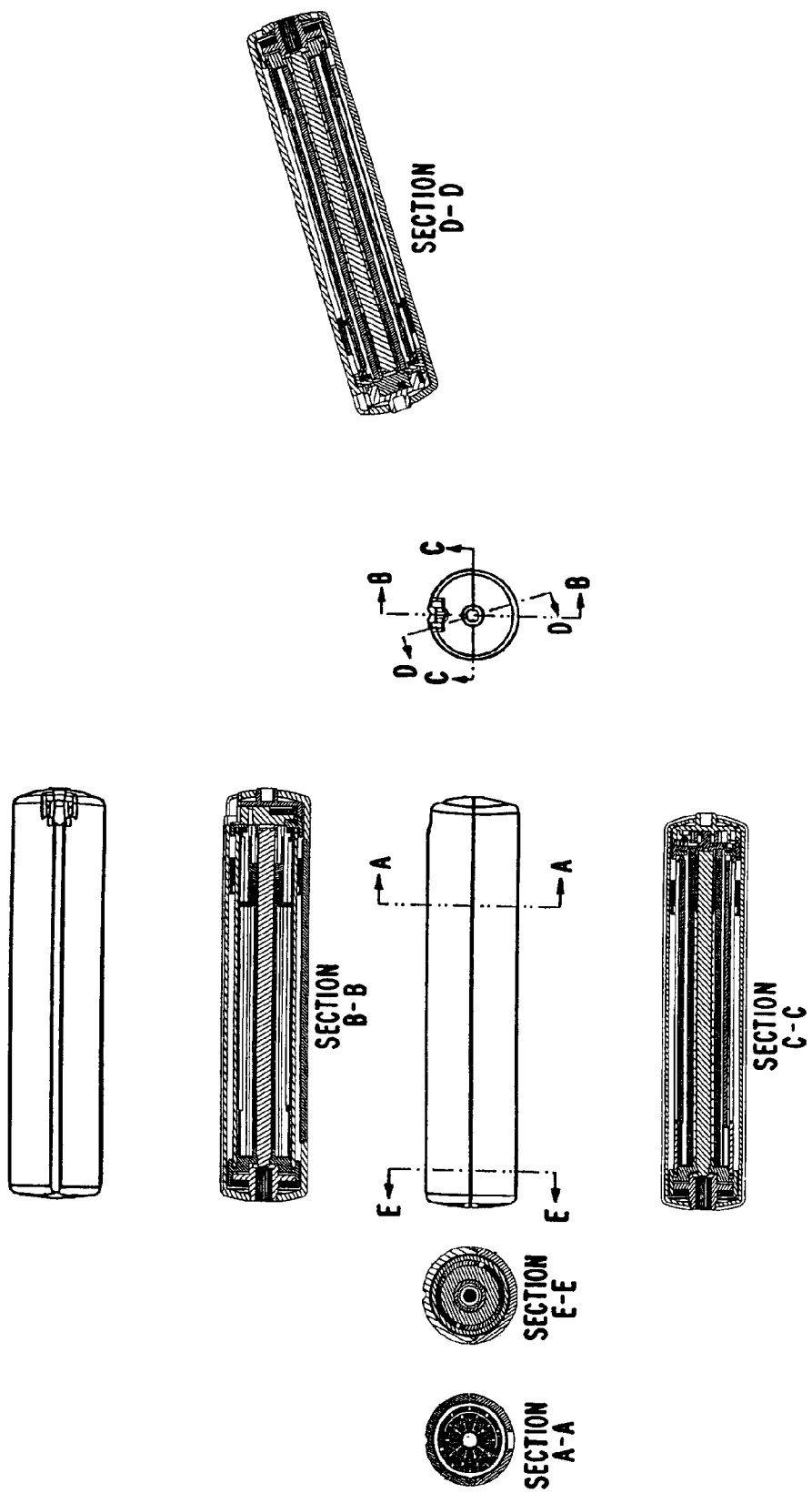
FIG. 13 shows the various sectional locations for FIGS. 14–18 with respect to the cartridge, according to the present invention.

FIG. 31 shows the components making up the barrel index assembly 2 of FIG. 12. The barrel index assembly 2 initiates the rotation of the cartridge so as to provide seeds to a medical instrument. The medical instrument is not shown in FIG. 31 (but see FIG. 51), but it is configured to receive a seed from the shuttle 316 when the shuttle 316 is in the fully-extended position, to thereby provide the seed to the medical instrument in which the cartridge is inserted. The seed in then inserted into the patient's body by way of the medical instrument.

Figure 36A:
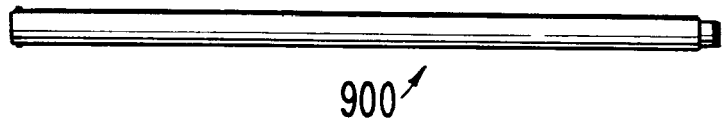
FIGS. 36A–C show different views of a center shaft or center rod, according to the present invention.
Figure 36B:
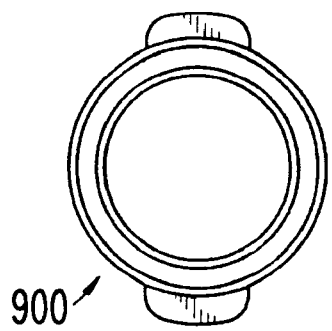
Figure 36C:
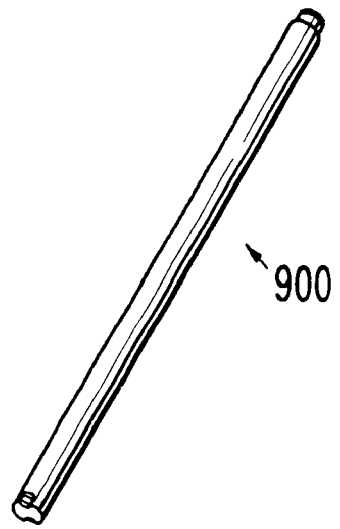

As seen in FIG. 31, the distal cap 311 is press fitted with the end of the center shaft 900 that has a flange 905 to thereby perform the press fit (see also FIGS. 36A–36C). FIG. 32 shows a hole 3260 that is provided in the middle of the distal cap 311, and in which the center shaft 900 is rigidly fitted therein (by way of the side opposite to the side shown in FIG. 32B).

Figure 34A:
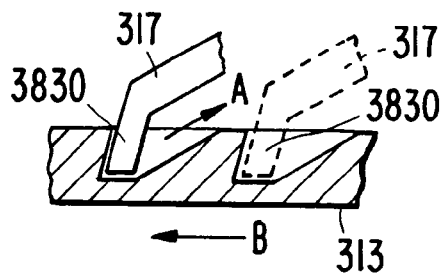
FIGS. 34A–D show different views of a ratchet disk, according to the present invention.
Figure 34B:
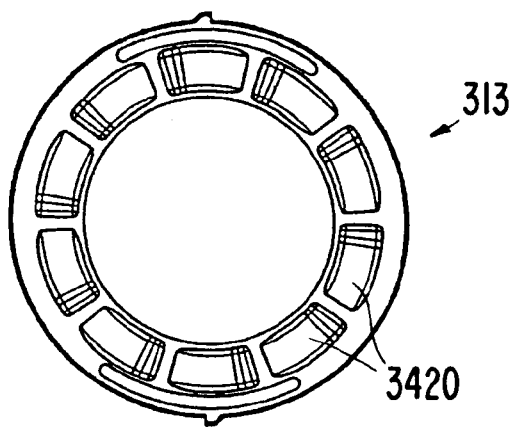
Figure 34C:
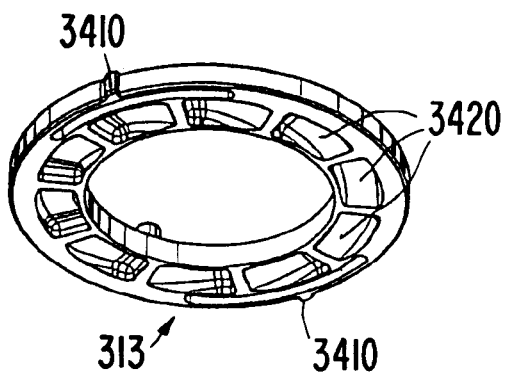

Also shown in FIG. 31 is a disk ratchet 313. The disk ratchet 313 has two tabs 3410 on its outer perimeter, as seen best in FIGS. 34B and C. The disk ratchet 313 is preferably a plastic part. The two tabs 3410 are squeezed together so that are received into two oppositely-positioned grooves 3270 (see FIG. 31) of the distal cap 311, so that the disk ratchet 313 is fitted for common movement with the distal cap 311 and so that the disk ratchet 313 can only rotate in one direction. FIGS. 34B and 34C show ten counterbores 3420 on one side of the disk ratchet 313. Each of the counterbores 3420 is ramped (see FIGS. 34A and B in particular), to only allow rotation in one direction, to be explained in more detail below. The pins 3430 on the other side of the disk ratchet 313 fit into holes (not shown) provided on the proximal end (outer diameter portion) of the shield barrel 13, in order to couple the two elements together for common movement.

Figure 11:
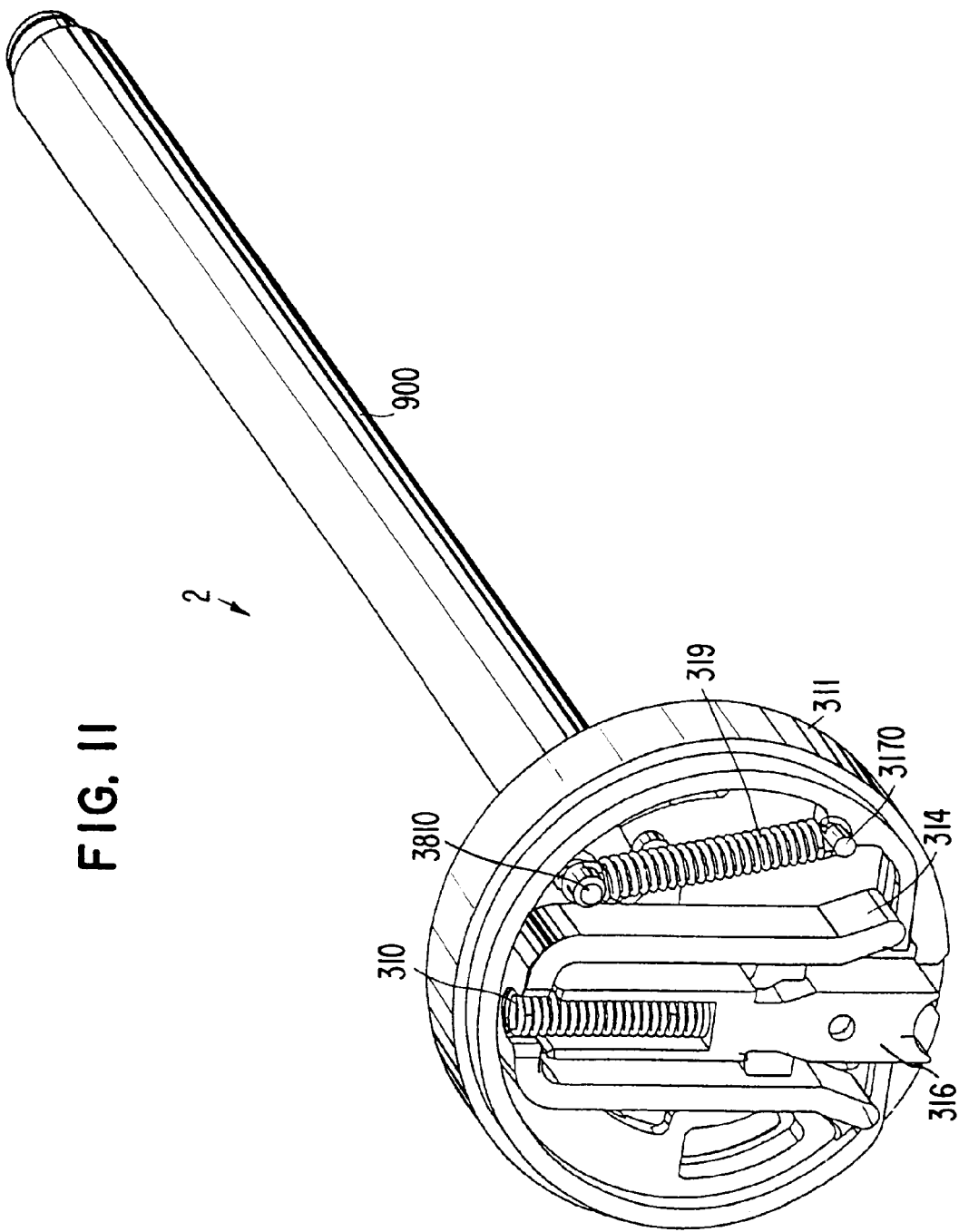
FIG. 11 is a perspective view from the same location as given in FIG. 10, but with a shuttle cover removed to show the positioning of a shuttle and a shuttle lock within the cartridge, according to the present invention.

FIG. 11 shows the distal cap 311 with the shuttle cover off, where an extension spring 319 is shown having one end connected to a pin 3170 of the distal cap 311 (see FIG. 32C), and having another end connected to a pin 3810 of the slider ratchet 317 (see FIG. 38B), and where the extension spring 319 urges the slider ratchet 317 to move in a clockwise direction. A protruding arm of the shuttle 316 prevents the slider ratchet 317 from moving in the clockwise direction when the shuttle 316 is in the fully-retracted position, as shown in FIG. 11.

Figure 10:
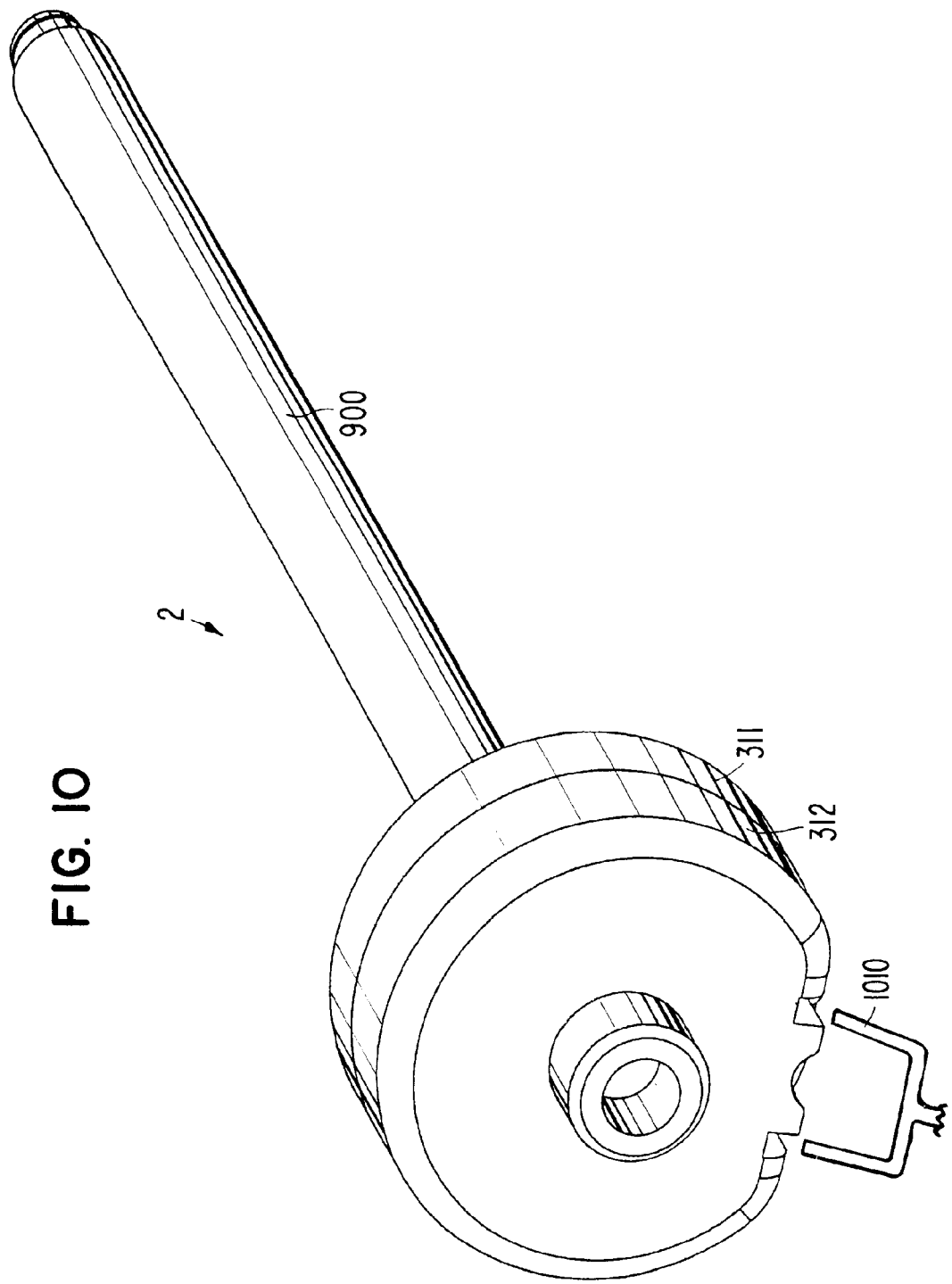
FIG. 10 is a perspective view from a different direction that that provided in FIG. 9.

FIG. 10 is the same view direction as in FIG. 11, but with the shutter cover 312 on. Also shown in FIG. 10 are two prongs of a tool 1010 of a medical instrument in which the cartridge is fitted into to thereby provide seeds to the medical instrument. The two prongs of the tool 1010 move upwards into openings in the bottom of the shuttle cover 312, whereby the two prongs pull apart ends of a shuttle lock 314, to thereby release a shuttle 316 to allow the shuttle to extend downwards to a fully extended position. This will be explained later in more detail. The shuttle cover 312 also acts as a backboard for the shuttle 316, whereby when seeds are inserted from a conduit of the internal barrel 3 and into a hole of the shuttle 316 disposed within the shuttle cover 312, the seeds go into the hole of the shuttle 316, hit against an interior surface of the shuttle cover 312 that is directly behind the hole of the shuttle 316, and thereby stay in place within the hole of the shuttle 316. Once inside the hole of the shuttle 316, the seed can then be extended outwards from the cartridge by releasing the shuttle lock 314 that holds the shuttle 316 in a fully retracted position.

Referring back to FIGS. 32A–C, there is provided a slot extending in the up-and-down direction in middle of the distal cap 311, whereby the slot creates a top opening 3210 and a bottom opening 3220 with respect to the center shaft 900. Seeds are transferred one at a time through the top opening 3210 of the distal cap 311, and into the shuttle 316. The seeds are prevented from entering the bottom opening 3220 due to a washer 314 having only one hole 3910 positioned with the top opening (see FIGS. 39A–C). The washer 314 is positioned between the seeds and the distal cap 311, and held in place by way of its inserts 3920 fitting into slots of the distal cap 311 (see also FIG. 31 that shows the slots of the distal cap 311).

Figure 47:
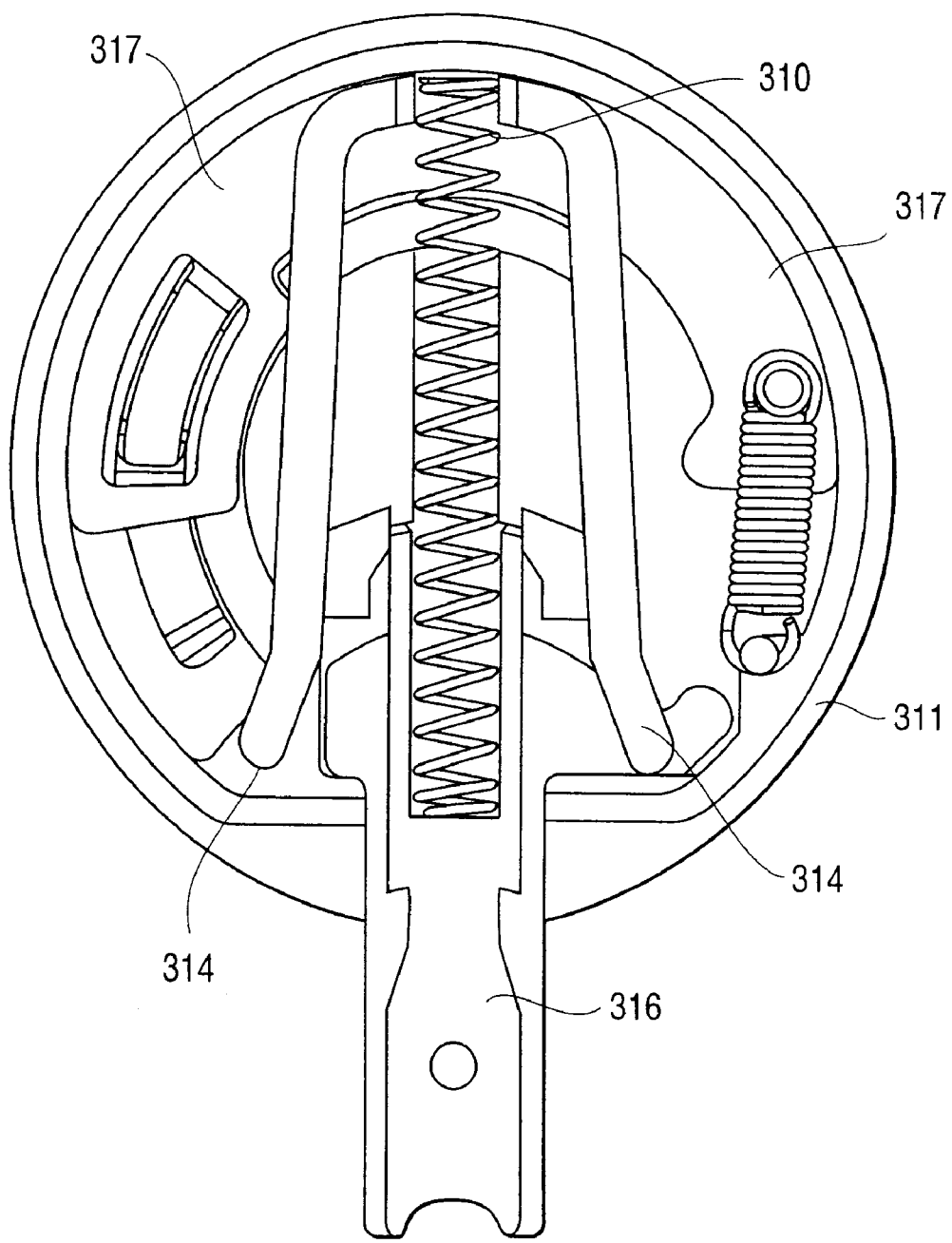
FIG. 47 is a view similar to that shown in FIG. 45, which shows the shuttle in the fully extended position, according to the present invention.
Figure 48:
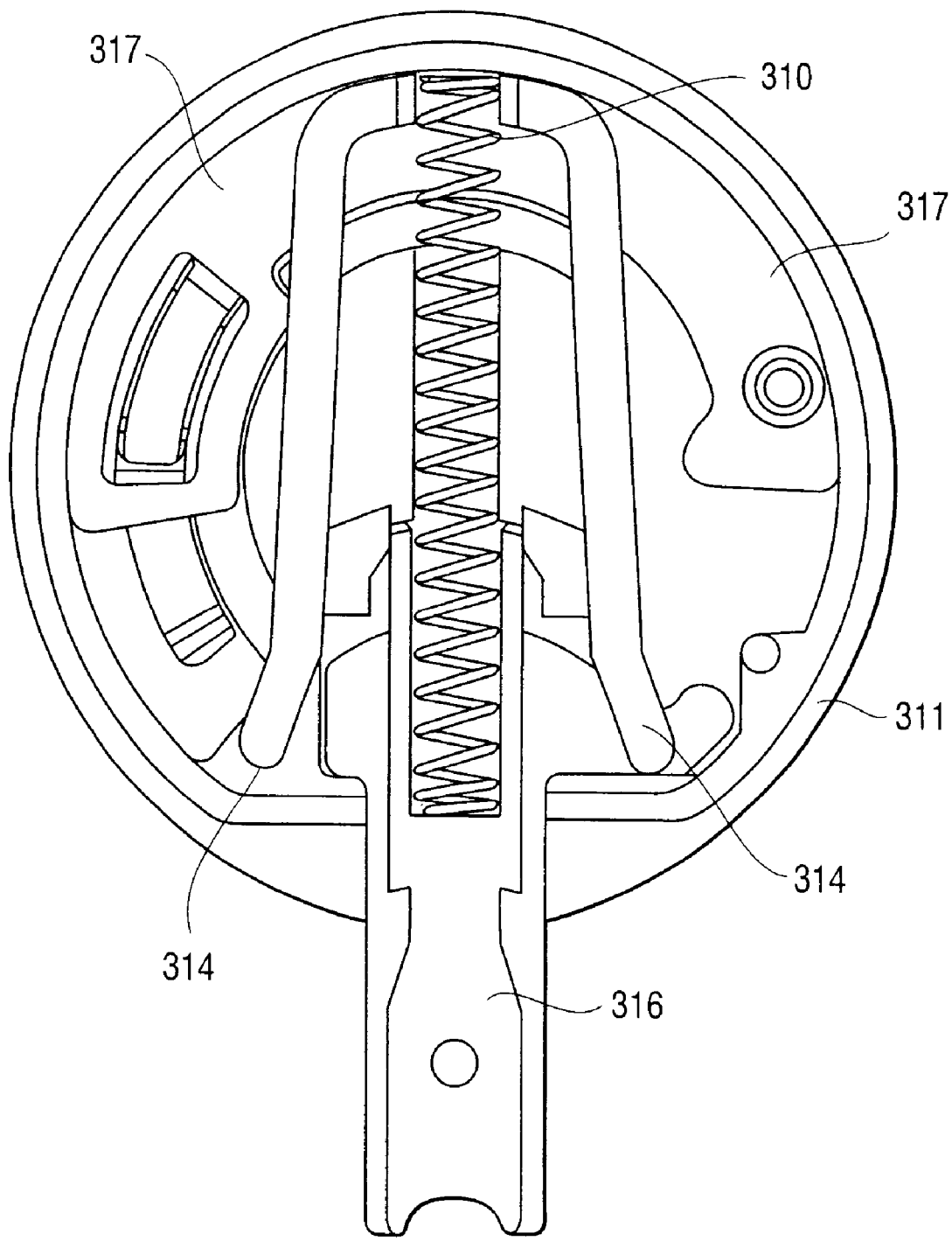
FIG. 48 is a view similar to that shown in FIG. 47, but with the extension spring removed for sake of clarity, according to the present invention.
Figure 49:
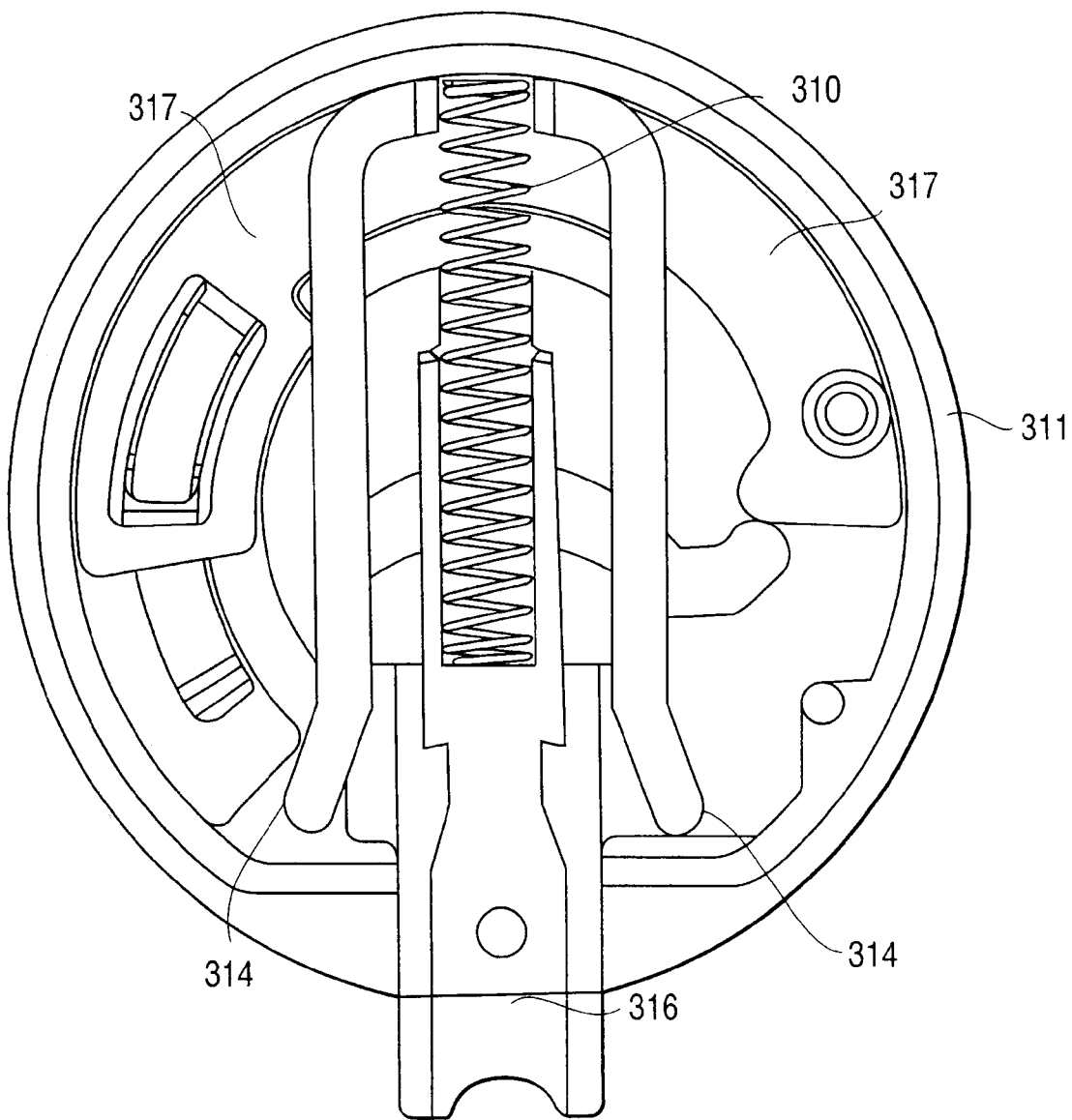
FIG. 49 is a view similar to that shown in FIG. 47, which shows the shuttle being reset back to the home position and how the shuttle pushes against the cam of the ratchet disk to force the ratchet disk to move counterclockwise, and with the extension spring removed for sake of clarity, according to the present invention.

Shuttle 316 is disposed so as to accept a seed and to extend outwards (upwards as shown in FIG. 31, but actually the shuttle 316 extends downwards when the cartridge is properly positioned within the medical instrument, as seen in FIGS. 47–49, for example), so that the shuttle (with the seed disposed therein) extends out of the housing 10 and into a seed-accepting region of a medical instrument in which the cartridge is positioned.

Figure 2:
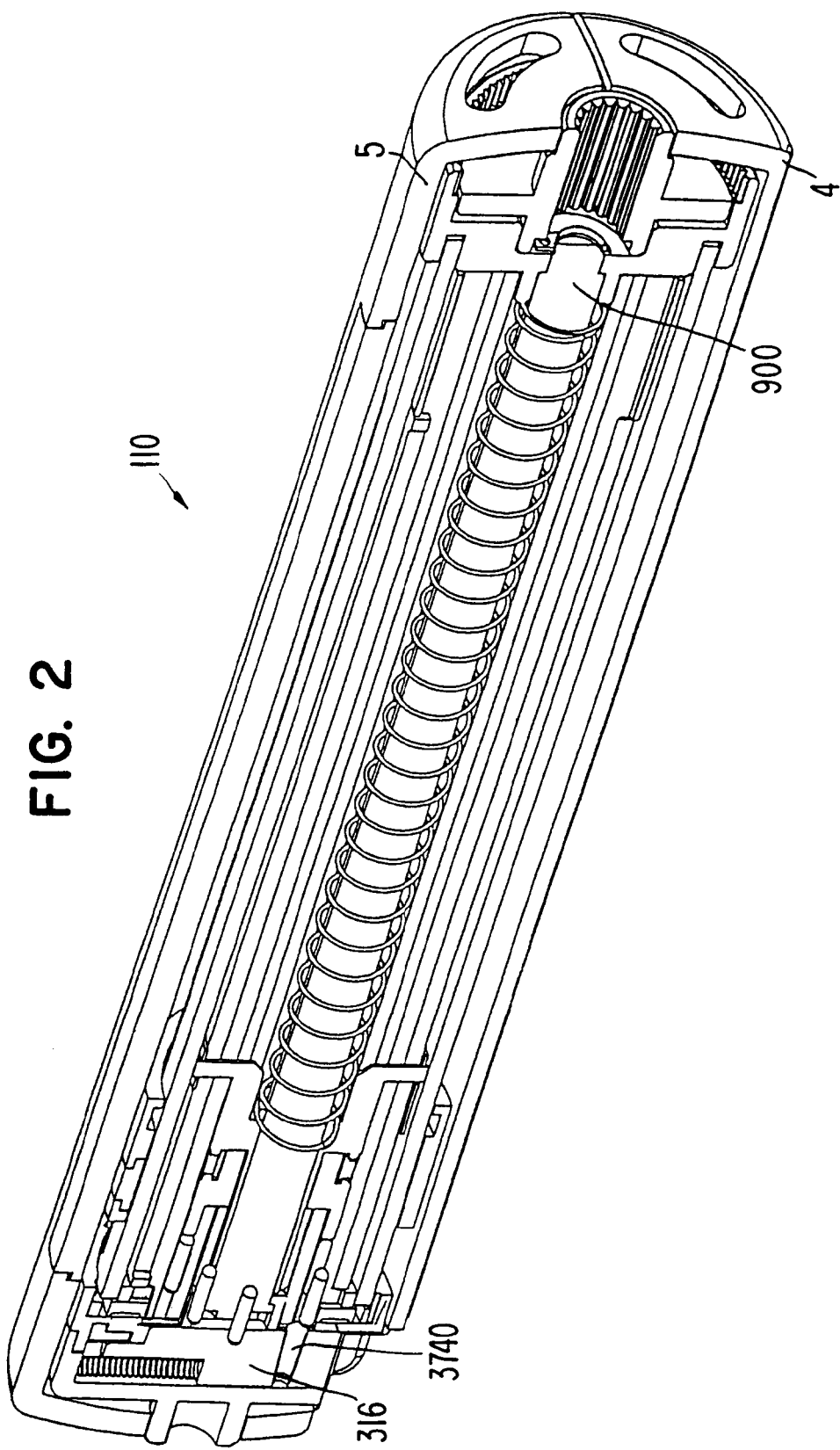
FIG. 2 is a cutaway view that shows various elements within the outer housing of the cartridge, according to the present invention.

Since the shuttle 316 has to be as close as possible to the opening of the internal barrel, see FIG. 2, for example, there is required a top and bottom opening of the distal cap 311, to provide for the required amount of extension, or stroke, of the shuttle 316 out of the housing 110. Other configurations may not require such a long shuttle extension, and for those configurations, only one opening in the distal cap 311 may be all that is needed.

Figure 43:
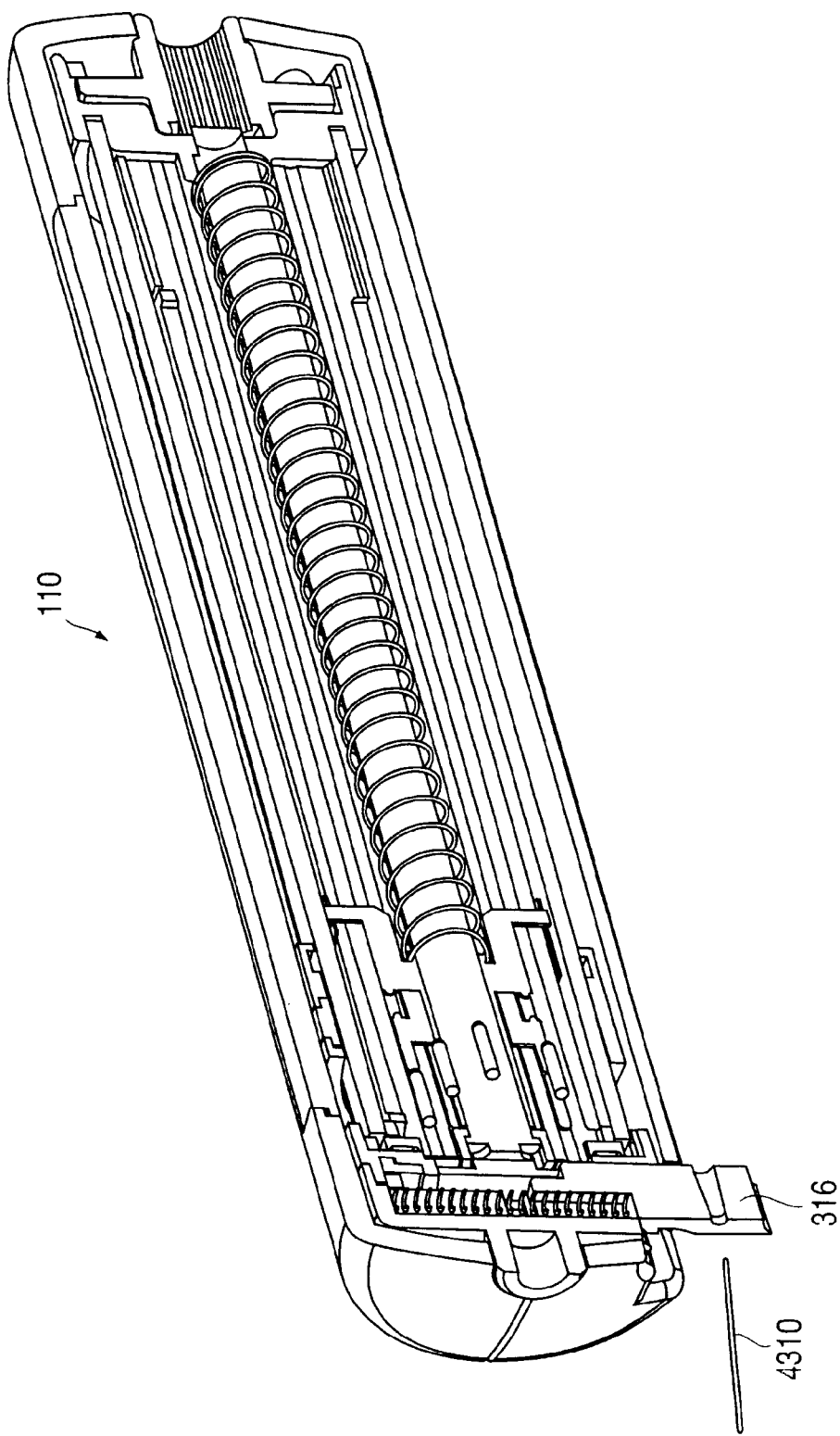
FIG. 43 is a cutaway view similar to the one shown in FIG. 2, but with the shuttle in the fully-extended position.
Figure 44:
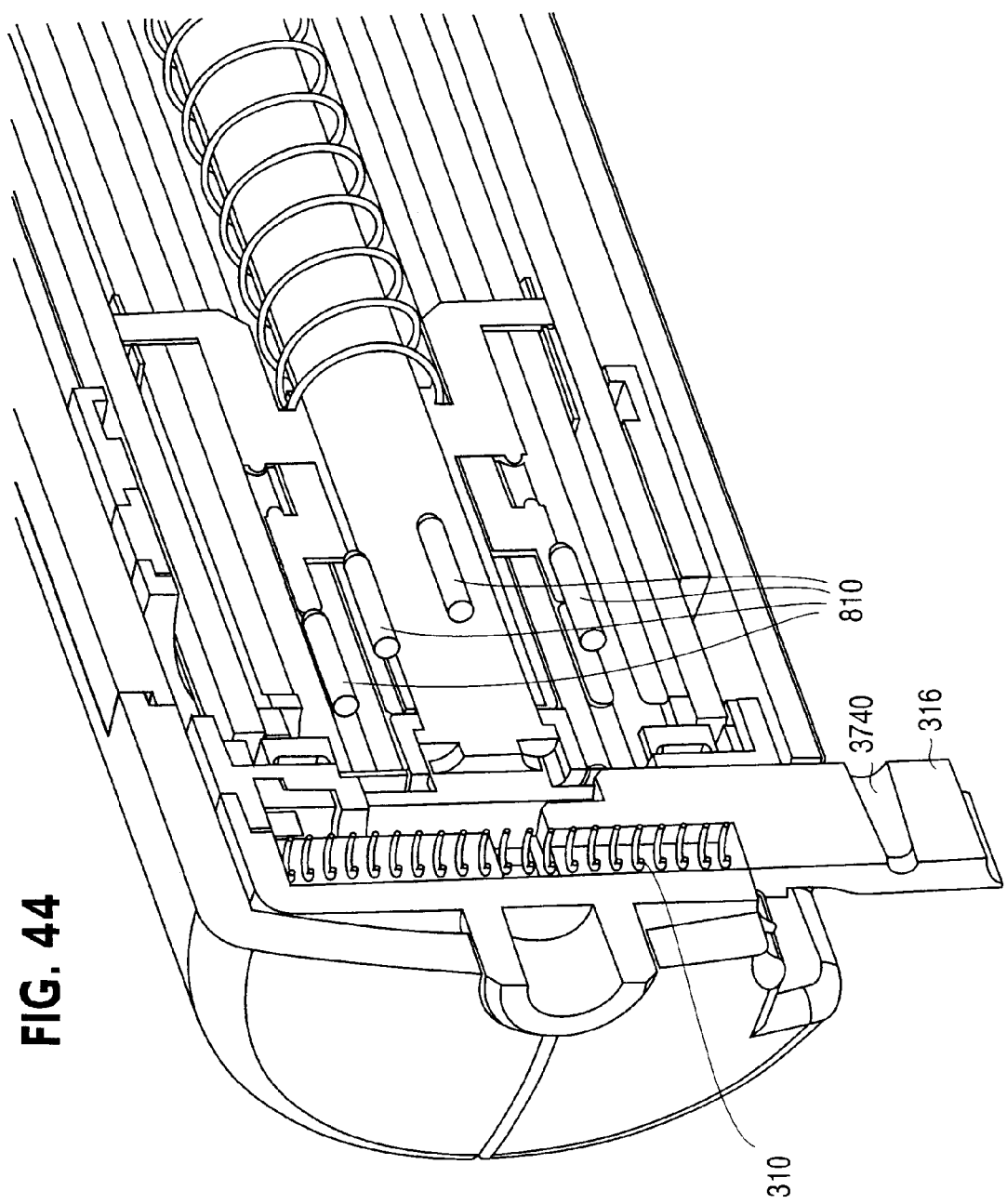
FIG. 44 is a blow-up of the region of FIG. 43 where the fully-extended shuttle is disposed.
Figure 45:
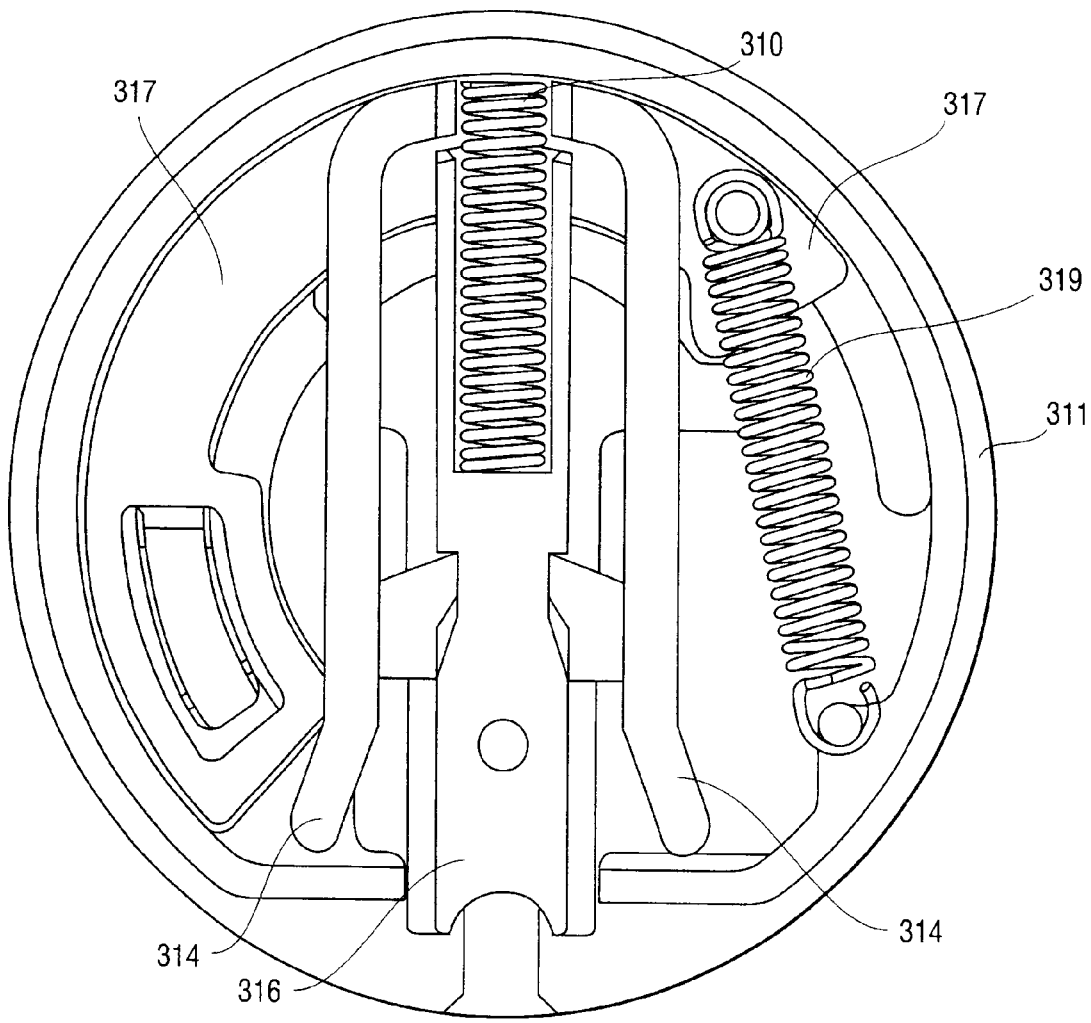
FIG. 45 is a view similar to that shown in FIG. 11, but which provides a view directly into the shuttle cover to show the relationship of the ratchet disk and the shuttle when the shuttle is in the home or fully retracted position, according to the present invention.

Referring now to FIG. 2, the shuttle 316 receives a seed from a bottom-most conduit of the internal barrel 3, where that seed is held within a tapered hole 3740 of the shuttle 316. In the preferred embodiment, the hole 3740 is tapered outwards slightly as it gets closer to the internal barrel 3, so that any minor misalignment of the conduits or channels of the internal barrel 3 with respect to the shuttle 316 will still allow for the seed to be accepted into the hole 3740 of the shuttle 316. In FIG. 2, the shuttle 316 extends downwards, and out of the bottom housing 4, with the shuttle 316 being shown in its extended position in FIG. 43. While FIG. 31 shows the shuttle positioned in an opposite direction, that is just for clarity sake, and the preferred position is for the shuttle 316 to extend downwards. FIGS. 43 and 44 show the shuttle 316 at its fully-extended position. This position is achieved by an operator pressing a button, switch, trigger or the like on the medical instrument to thereby provide a seed from the cartridge to the medical instrument. Once the seed is provided from the cartridge to the medical instrument, the seed can then be provided to a patient, by way of another activation of the medical instrument.

Shuttle spring 310 biases the shuttle 316 downwards, whereby the shuttle is kept in place within the housing 110 by way of the shuttle lock 314. In more detail, referring to FIGS. 35A and 35B, the shuttle lock 314 has teeth 3510 that hold the shuttle 316 in place when the shuttle is fully retracted. The shuttle lock 314 releases the shuttle 316 when a command is made for a seed to be provided from the cartridge to the medical instrument.

The shuttle 316 is preferably a sintered MIM part, so as to provide a radioactive shield to protect users when a seed is disposed in the hole 3740 of the shuttle 316, since then the seed is exterior with respect to the shield barrel 13 and the tube-scale 16.

Figure 32A:
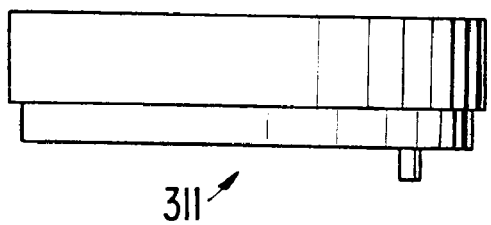
FIGS. 32A–C show different views of a distal cap, according to the present invention.
Figure 32B:
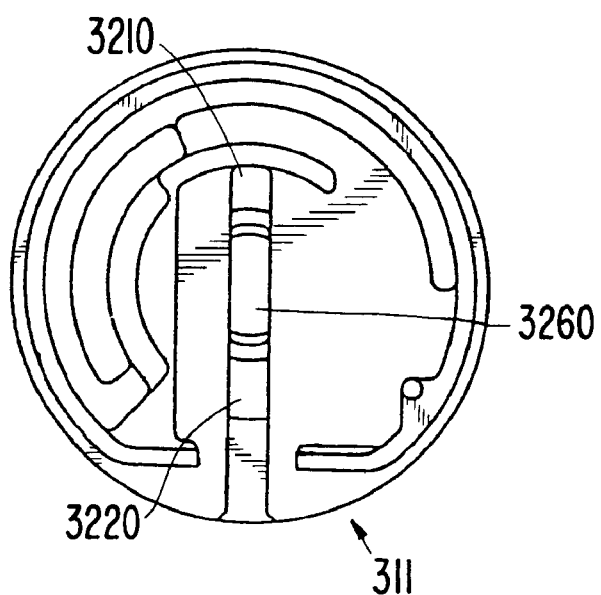
Figure 32C:
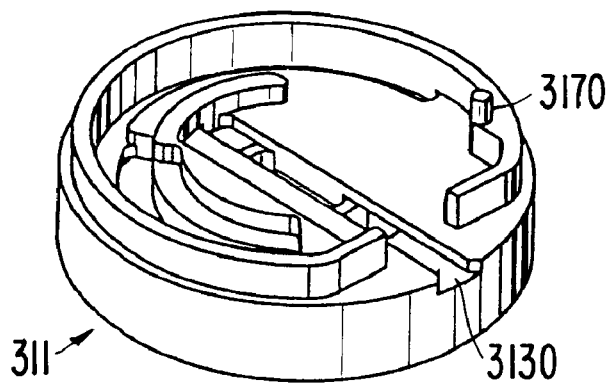
Figure 33A:
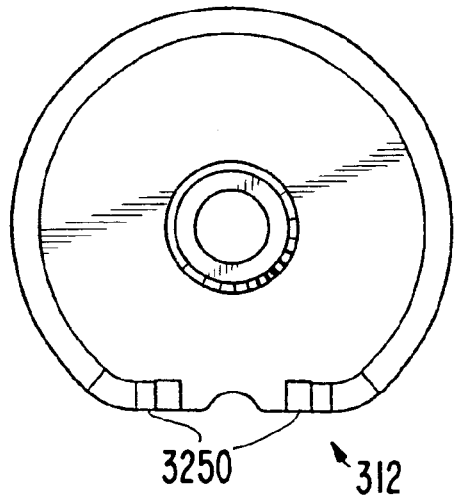
FIGS. 33A–C show different views of the shuttle cover, according to the present invention.
Figure 33B:
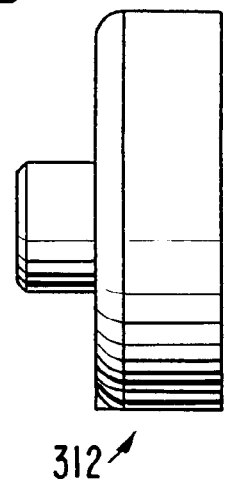
Figure 33C:
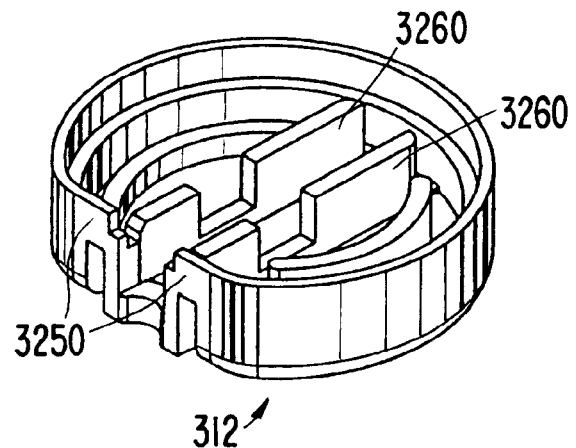
Figure 37A:
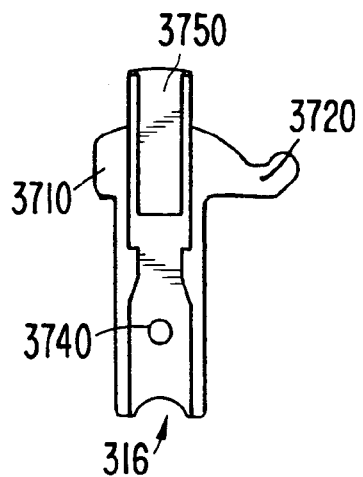
FIGS. 37A–C show different views of the shuttle, according to the present invention.
Figure 37B:
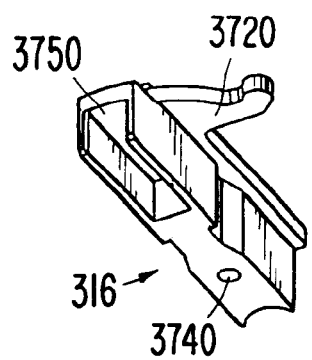
Figure 37C:
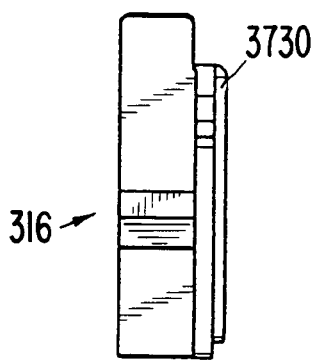
Figure 46:
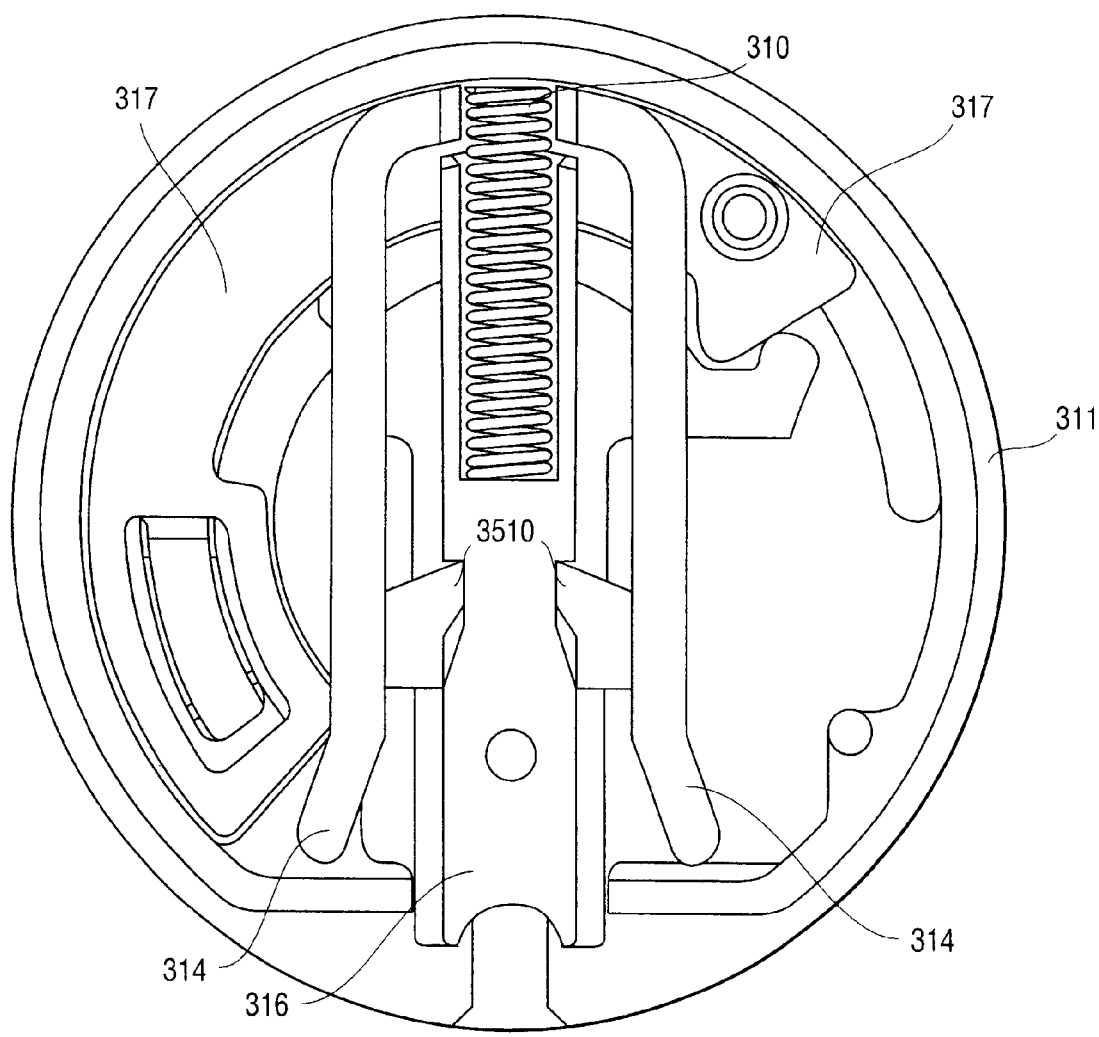
FIG. 46 is a view similar to that shown in FIG. 45, but with an extension spring removed for sake of clarity, in order to show how an extension arm of the shuttle urges the ratchet disk counterclockwise by way of pushing against a cam of the ratchet disk, according to the present invention.

The shuttle 316 slides within a slot of the distal cap 311, which corresponds to slot 3130 as shown in FIGS. 32A–C. In particular, a protruding ledge 3720 of the shuttle 316 (see FIGS. 37A–C) fits within the slot 3130 of the distal cap 311, to allow the shuttle 316 to slide up and down within the slot 3130. As the shuttle 316 slides up and down, it can go between a fully retracted, or home position, to a fully extended position. FIGS. 37A–C also show that the shuttle 316 has an opening 3750 in which a shuttle spring 310 is placed, where the shuttle spring 310 urges the shuttle 316 downwards towards its fully extended position, but where the shuttle lock 314 keeps the shuttle 316 in place by way of the teeth 3510 of the shuttle lock 314 fitting into indentations on respective sides of the shuttle 316 (see FIG. 46 in particular). FIG. 37A also shows that the shuttle 316 has a second protruding ledge 3710, which is smaller than the first protruding ledge 3720. The first and second protruding ledges 3710, 3720 keep the shuttle from flying out of the shuttle cover 312 when the shuttle is released by the shuttle lock 314 and the shuttle spring 310 fires the shuttle 316 to its fully extended position. In more detail, the first and second protruding ledges 3710, 3720 hit against the bottom parts 3250 of the shuttle cover 312 (see FIGS. 33A–C) to thereby keep the shuttle 316 within the shuttle cover 312 after it is fired outwards by the force of the shuttle spring 310.

Figure 39A:
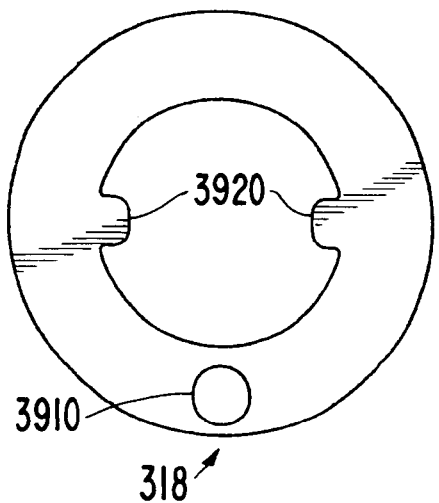
FIGS. 39A–C show different views of a spacer or washer, according to the present invention.
Figure 39B:
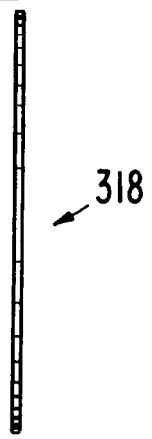
Figure 39C:
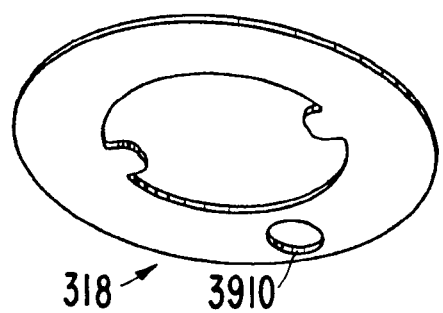
Figure 41A:
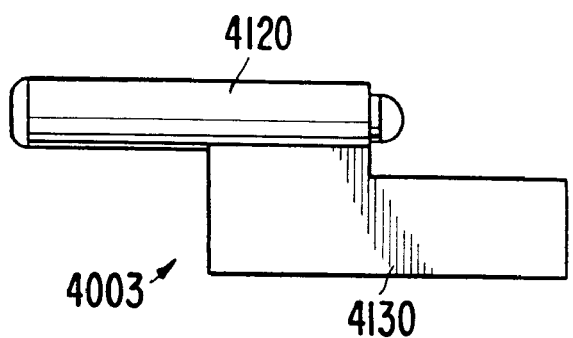
FIGS. 41A–C show different views of a seed pusher of the cartridge, according to the present invention.
Figure 41B:
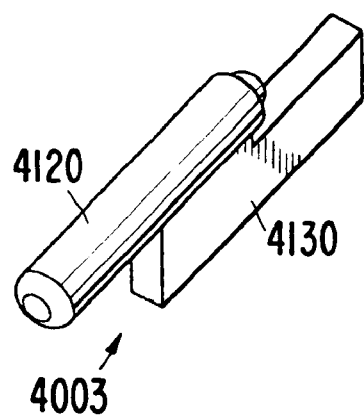
Figure 41C:
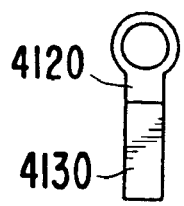

Referring back to FIGS. 37A–C, the shuttle 316 also has a hole 3740, which is sized to accept a seed, and which is positioned behind the top opening 3210 of the distal cap 311 (see FIGS. 32A–C) and the hole 3910 of the washer 318 (see FIGS. 39A–C). When a seed is fired out from a conduit of the internal barrel 3, the seed passes through the hole 3910 of the washer 318, then through the top opening 3210 of the distal cap 311, and then into the hole 3740 of the shuttle 316. The distal cap 311 also has a bottom opening 3220, but where the washer 318 blocks a seed from passing through a conduit of the internal barrel 3 that faces that bottom opening 3220.

In the present invention, the stroke of the shuttle 316 (the distance between the home position and the fully-extended position) has to be large enough to get the shuttle 316 and the seed within it to a position that is exterior with respect to the outer housing 120 of the cartridge. Once the shuttle 316 is in its fully extended position, a user can activate the medical instrument to remove the seed from the shuttle 316, and thereby provide the seed to the medical instrument, in order to then insert the seed into the patient's body. For example, FIG. 43 shows a pusher element 4310 of the medical instrument, which pushes the seed out of the hole of the fully extended shuttle 316 and into a particular location within the medical instrument.

To keep the seed in oppositely-positioned chamber from extending into the lower opening 3220 of the distal cap 311 when the shuttle 316 moves to the fully extended position, and thereby keep the cartridge from jamming due to the shuttle 316 not being able to go back to the home position because of the seed disposed in its downward path, the washer 318 is provided. The washer 318 is preferably a stainless steel part and is fairly thin, and in which washer 8 and has only one hole 3910 in its ring portion The washer 318 is provided to close the channel in the oppositely-positioned (12 o'clock position) chamber of the internal barrel 3. The washer 318 is fitted within slots of the distal cap 311 to lock those elements in place with respect to each other. Note that the washer 318 should be shown as being to the right of the distal cap 311 and to the left of the disk ratchet 313 in FIG. 31, since that is the correct position when the elements are coupled together to form the barrel index assembly 2.

Figure 35A:
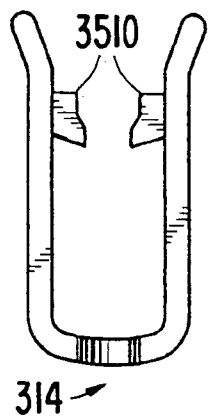
FIGS. 35A–C show different views of the shuttle lock, according to the present invention.
Figure 35B:
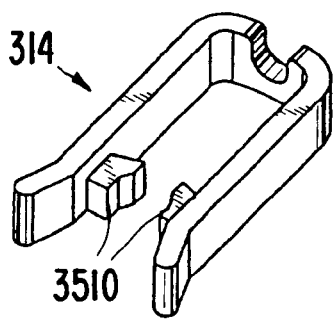
Figure 35C:

FIG. 11 shows the shuttle spring 310 trying to force the shuttle 316 downwards, but where the shuttle lock 314 keeps the shuttle 316 in place by way of its teeth 3510 and does not allow it to go downward. In the preferred embodiment, the shuttle lock 314 is a plastic part. The shuttle lock 314 is initiated by a tool 1010 (see FIG. 10) of the medical instrument in which the cartridge is placed to provide seeds to a patient. The tool 1010 has two prongs which respectively push against the two bottom portions of the shuttle lock 314 to thereby spread the respective sides of the shuttle lock 314 outwards. This releases the shuttle 316 from the shuttle lock 314, whereby the force of the shuttle spring 310 pushes the shuttle 316 downwards to the fully open position. See FIGS. 11, 31, 46 and 47 in particular. FIGS. 35A–C show other views of the shuttle lock 314, which includes the two fairly thick teeth 3510 that respectively engage recesses on opposite sides of the shuttle 316, and which take the load caused by the shuttle 316 being urged downward by the spring 310. The teeth 3510 are separated from the recesses of the shuttle 316 by way of the tool 1010 of the medical instrument. The shuttle lock 314 sits in place within two ribs 3260 of the shuttle cover 312, as seen best in FIG. 33C.

In more detail, the shuttle lock 314 is disposed between the distal cap 311 and the shuttle cover 312, as seen best in FIG. 11 and FIGS. 45–49. The shuttle lock 314 stays in position within the shuttle cover 312 when the shuttle 316 is ejected outwards to its fully extended position.

The outer housing 110 of the cartridge is preferably provided with a guide (e.g., a groove) on the outside of the housing, which allows the cartridge to be situated into the medical instrument at the correct orientation. When doctor wants to deliver the seed, he or she activates a button, trigger or the like on a medical instrument (with the cartridge in place within the medical instrument), which releases the shuttle from within the housing of the cartridge to outside of the housing and into a particular position within the medical instrument. The cartridge cannot be removed at that point, until the shuttle is reset. To reset the shuttle, a tool (not shown) pushes the shuttle 316 back within the housing 110 of the cartridge. Once the shuttle 316 is retracted, a pusher element (such as element 4310 as shown in FIG. 43) of the medical instrument is engaged upon another action by the doctor, which pushes the seed out of the hole of the fully-extended shuttle and into a particular position within the medical instrument. The seed is then ready to be inserted by the medical instrument into a particular region of the patient's body. The pusher element of the medical instrument retracts, and a tool of the medical instrument pushes the shuttle back down into the housing 120 and back to its home or fully retracted position, to be accepted by and held in place by the shuttle lock 314. These actions all occur due to the second action by the doctor to remove the seeds from the shuttle and into the medical instrument.

The distance between the seed-accepting hole 3740 of the shuttle 316 and the top-most part of the shuttle 316 should preferably be at least 0.040" stainless steel, to provide an ample amount radiation shielding when a seed is disposed within the seed-accepting-hole of the shuttle 316.

The mechanism for providing rotational movement of the cartridge, specifically the internal barrel 3 of the cartridge, will be explained in more detail below.

Figure 38A:
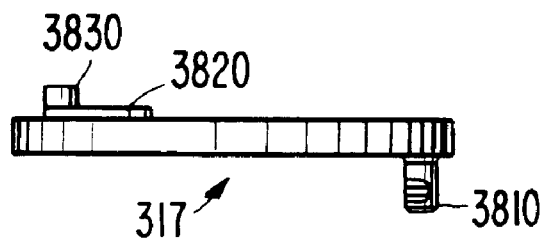
FIGS. 38A–C shows different views of a slider ratchet, according to the present invention.
Figure 38B:
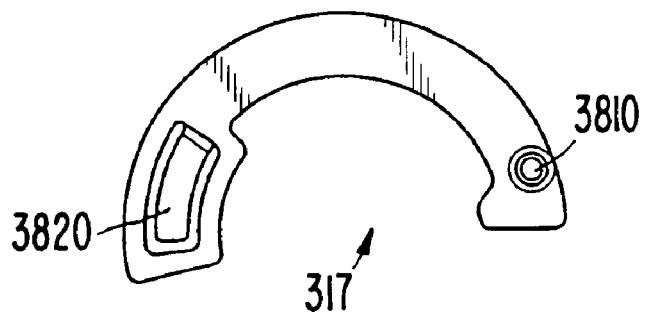
Figure 38C:
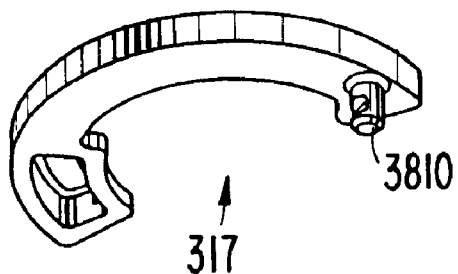

The slider ratchet 317 takes the motion off of the slider 14 to, rotate the internal barrel 3. There is provided an open space in the distal cap 311, by which a spring finger 3820 of the slider ratchet 317 extends in (see FIGS. 38A–C as well as FIG. 31). FIGS. 38A–C show the slider ratchet 317 in detail. The slider ratchet 317 includes a cantilevered finger 3820 with a protruding part 3830 on one end. The other end of the slider ratchet 317 includes a pin 3810 and a cam-shaped end part. The pin 3810 is configured to hold in place one end of an expansion spring 319, as seen best in FIGS. 45 and 46. As seen in FIGS. 34A–C, the disk ratchet 313 has ten counterbores 3410, each one is a ratchet tooth (female). With such a configuration, only one-directional movement is provided for the slider ratchet with respect to the disk ratchet, and hence the internal barrel 3 moves based on movement of the slider ratchet 317. In more detail, referring now to FIG. 34A, the protruding part 3830 of the finger 3820 of the slider ratchet 317 fits into one of the counterbores 3420 of the disk ratchet 313, and slides over to the next adjacent counterbore in the direction provided by the arrow A in FIG. 34A, when the shuttle 316 goes to its fully extended position. When the shuttle 316 is retracted back again, this pushes the disk ratchet 313 in a direction shown by the arrow B in FIG. 34B, thereby moving the entire cartridge assembly in that direction. The movement corresponds to a 36 degree rotation of the internal barrel 3.

These actions occur due to the following. The first protruding extension 3720 of the shuttle 316 (see FIGS. 37A–C) pushes against the bottom, cam-shaped surface of the right-portion of the slider ratchet 317 (See FIGS. 38A–C). Thus, in the home position, the shuttle 316 urges the bottom horizontal face of the right side of the slider ratchet 317 in a counter-clockwise direction, as seen best in FIG. 45 and 46. The right side of the slider ratchet 317 is moved so that its cam-shaped surface is approximately at a 45 degree position (see FIG. 46), whereby the first protruding part 3720 of the shuttle 316 pushes against that cam-shaped surface of the slider ratchet 317. As the shuttle 316 is released downwards to go to its fully extended position, the slider ratchet 317 is allowed to move clockwise, by way of the force applied in that direction by the expansion spring 319. The expansion spring 319 forces the cam surface of the slider ratchet 317 against the first protruding part 3720 of the shuttle 316 when the shuttle 316 is in the home position. That is, the expansion spring 319 urges the slider ratchet 317 to want to move in a clockwise direction, when viewed from FIGS. 45 and 46.

Figure 34D:
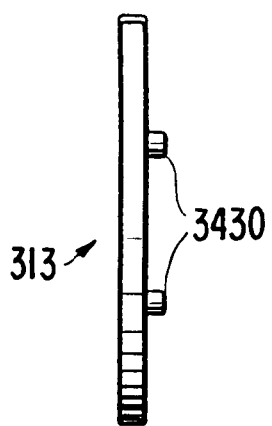

When the shuttle 316 is released from the shuttle lock 314 to thereby extend downwards, the slider ratchet 317 moves clockwise since the shuttle 316 is no longer provided in a location to counter the force applied by the expansion spring 319. The protruding part 3830 of the cantilevered finger 3820 of the slider ratchet 317 then moves up a ramp from one counterbore of the disk ratchet 313 to the next clockwise counterbore. Note that this action does not cause the internal barrel 3 to move. When the shuttle 316 is placed back in the home position (by way of the prongs on a tool of the medical instrument), the shuttle 316 pushes against the cam surface of the slider ratchet 317 to thereby move it in a counter-clockwise (and also overcoming the force of the expansion spring 319. This action moves the disk ratchet 313 in the counterclockwise direction since the protruding part 3830 of the slider ratchet 317 is pushing against the vertical wall of the counterbore of the disk ratchet 313 in which it is disposed (see FIG. 34A in particular). The movement of the disk ratchet 313 counterclockwise causes the internal barrel 3 to move counterclockwise in turn, since the pins 3430 of the other side of the disk ratchet 313 (see FIG. 34D) are fitted into respective holes of the shield barrel 13.

The disk ratchet 313 is fitted into the distal cap 311 in the cartridge assembly, by way of the tabs 3410 of the disk ratchet 313 (see FIGS. 34B and C) fitting into slots 3270 provided on the distal cap (see FIG. 31). When the disk ratchet 313 moves counterclockwise, this movement forces the distal cap 311 to move counterclockwise as well, thereby rotating the internal barrel 3 with respect to the center shaft 900 of the cartridge. Thus, the rotating of the internal barrel 3 is caused by the resetting of the shuttle 316 back from its fully extended position to its home, or fully closed position.

While the above components are described with respect to the preferred embodiment, other similar types of components may be utilized, while remaining within the spirit and scope of the present invention, as exemplified by the claims. For example, for a cartridge in which verification and calibration are not needed, only a single radiation shield would be required, which would be a cylindrically-shaped tube with no slots or channels provided on it.

What is claimed is:

1. A cartridge for a medical instrument, comprising:

an internal barrel having a plurality of conduits for receiving seeds to be applied to a patient by way of the medical instrument;

a center shaft on which the internal barrel rotates; and a shuttle that accepts one seed from one of the plurality of conduits of the internal barrel, wherein the internal barrel rotates so as to provide seeds from each of the plurality of conduits to the shuttle, one at a time in sequence, and wherein the shuttle is extendable away from said cartridge to provide each of the seeds, one at a time, to the medical instrument.

2. The cartridge according to claim 1, further comprising:

a first shield barrel that includes a plurality of slots, and that provides radioactive shielding to an exterior of the cartridge due to the seeds being radioactive; and a second shield barrel that includes a plurality of slots, and that provides radioactive shielding to the exterior of the cartridge, wherein the slots of the first and second shield barrels are aligned in a first mode of the cartridge, so as to provide radiation through the respective slots to the exterior of the cartridge in a verification or calibration procedure, and wherein the slots of the first and second shield barrels are not aligned in a second mode of the cartridge, so as to block radiation from passing to the exterior of the cartridge.

3. The cartridge according to claim 2, wherein the first and second shields are made of stainless steel.

4. The cartridge according to claim 2, wherein the second mode is a normal mode of the cartridge, and wherein the cartridge can only be set to the first mode by manipulating the cartridge.

5. The cartridge according to claim 2, further comprising:

a proximal cap; and a distal cap, wherein the proximal and distal caps are provided on respective proximal and distal ends of the cartridge, and which block radiation from exiting from the proximal and distal ends to the exterior when seeds are disposed within the cartridge.

6. The cartridge according to claim 1, further comprising:

a shield barrel that provides a radioactive shielding for the cartridge, the shield barrel encompassing the internal barrel and being provided with a plurality of numeric indicators on an outer surface thereof;

an indicator ring that is coupled to the shield barrel and that moves in accordance with rotation of the internal barrel and that is positioned with respect to a last seed deposited into the internal barrel; and an outer housing that encompasses the shield barrel and that includes an opening that allows a user to view one of the numeric indicators that is positioned directly below the indicator ring, so as to determine a current remaining number of seeds in the cartridge.

7. A cartridge for a medical instrument, comprising:

a means for receiving seeds, wherein the seeds are to be applied to a patient by way of the medical instrument;

a means for rotating on which the means for receiving seeds rotates; and a means for accepting seeds from the means for receiving seeds, wherein the means for accepting seeds is extendable away from said cartridge to provide each of the seeds, one at a time, to the medical instrument.

8. The cartridge for a medical instrument according to claim 7, wherein the means for receiving seeds comprises an internal barrel having a plurality of conduits.

9. The cartridge for a medical instrument according to claim 7, wherein the means for rotating comprises a center shaft.

10. The cartridge for a medical instrument according to claim 7, wherein the means for accepting seeds comprises a shuttle that accepts seeds from the means for receiving seeds.

* * * * *